(12) United States Patent
Keller et al.

(10) Patent No.: US 12,667,731 B2
(45) Date of Patent: Jun. 30, 2026

(54) BIOSTIMULATOR HAVING FLEXIBLE CIRCUIT ASSEMBLY

(71) Applicant: Pacesetter, Inc., Sylmar, CA (US)

(72) Inventors: Wade Keller, Aliso Viejo, CA (US); Thomas B. Eby, Mountain View, CA (US); Sean McKenna, Belmont, CA (US); Brett C. Villavicencio, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 18/649,836

(22) Filed: Apr. 29, 2024

(65) Prior Publication Data

US 2024/0278025 A1 Aug. 22, 2024

Related U.S. Application Data

(63) Continuation of application No. 17/565,325, filed on Dec. 29, 2021, now Pat. No. 11,969,604, which is a
(Continued)

(51) Int. Cl.
*A61N 1/375* (2006.01)

(52) U.S. Cl.
CPC ....... *A61N 1/37512* (2017.08); *A61N 1/3754* (2013.01); *A61N 1/3756* (2013.01); *A61N 1/3758* (2013.01)

(58) Field of Classification Search
CPC .............. A61N 1/37512; A61N 1/3754; A61N 1/3756; A61N 1/3758; A61N 1/378;
(Continued)

(56) References Cited

U.S. PATENT DOCUMENTS

| | | | |
|---|---|---|---|
| 4,929,409 A | 5/1990 | Agren et al. | |
| 5,224,023 A | 6/1993 | Smith et al. | |

(Continued)

FOREIGN PATENT DOCUMENTS

| | | |
|---|---|---|
| CN | 102711908 A | 10/2012 |
| CN | 107106853 A | 8/2017 |

(Continued)

OTHER PUBLICATIONS

International Preliminary Report on Patentability received for PCT Patent Application No. PCT/US2019/062265, mailed on Jun. 3, 2021, 10 pages.
(Continued)

*Primary Examiner* — Catherine M Voorhees
(74) *Attorney, Agent, or Firm* — WOMBLE BOND DICKINSON (US) LLP

(57) ABSTRACT

A biostimulator, such as a leadless cardiac pacemaker, having a flexible circuit assembly, is described. The flexible circuit assembly is contained within an electronics compartment between a battery, a housing, and a header assembly of the biostimulator. The flexible circuit assembly includes a flexible substrate that folds into a stacked configuration in which an electrical connector and an electronic component of the flexible circuit assembly are enfolded by the flexible substrate. An aperture is located in a fold region of the flexible substrate to allow a feedthrough pin of the header assembly to pass through the folded structure into electrical contact with the electrical connector. The electronic component can be a processor to control delivery of a pacing impulse through the feedthrough pin to a pacing tip. Other embodiments are also described and claimed.

19 Claims, 14 Drawing Sheets

Related U.S. Application Data continuation of application No. 16/687,477, filed on Nov. 18, 2019, now Pat. No. 11,247,059.

(60) Provisional application No. 62/770,088, filed on Nov. 20, 2018.

(58) Field of Classification Search
CPC ...... A61N 1/362; A61N 1/0587; H05K 1/189; H05K 2201/10015; H05K 2201/10151; H05K 2201/10174; H05K 2201/10545; H05K 2201/056; H05K 2201/10037; H05K 2201/10166; H05K 2201/10189; A61B 2560/04
See application file for complete search history.

(56) References Cited

U.S. PATENT DOCUMENTS

| | | | |
|---|---|---|---|
| 5,645,586 A | 7/1997 | Meltzer | |
| 5,814,090 A * | 9/1998 | Latterell | A61N 1/375 607/36 |
| 6,245,092 B1 * | 6/2001 | Schaldach, Jr. | A61N 1/37512 607/1 |
| 6,305,944 B1 | 10/2001 | Henry et al. | |
| 6,658,296 B1 * | 12/2003 | Wong | A61N 1/375 607/9 |
| 6,665,191 B2 | 12/2003 | Blood et al. | |
| 6,762,942 B1 | 7/2004 | Smith | |
| 7,211,884 B1 | 5/2007 | Davis et al. | |
| 8,639,341 B2 | 1/2014 | Sommer et al. | |
| 10,029,107 B1 | 7/2018 | Webb et al. | |
| 10,434,300 B2 | 10/2019 | Maile et al. | |
| 11,247,059 B2 * | 2/2022 | Keller | A61N 1/3754 |
| 11,969,604 B2 * | 4/2024 | Keller | A61N 1/3754 |
| 2003/0048621 A1 | 3/2003 | Blood et al. | |
| 2004/0075349 A1 | 4/2004 | Boss et al. | |
| 2004/0176818 A1 | 9/2004 | Wahlstrand et al. | |
| 2005/0056457 A1 | 3/2005 | Gall et al. | |
| 2008/0184554 A1 | 8/2008 | Degieux et al. | |
| 2010/0076533 A1 | 3/2010 | Dar et al. | |
| 2011/0190842 A1 * | 8/2011 | Johnson | A61N 1/375 600/561 |
| 2012/0151758 A1 | 6/2012 | Primavera | |
| 2012/0165902 A1 | 6/2012 | Sommer et al. | |
| 2015/0066115 A1 * | 3/2015 | Bunyan | A61N 1/3754 607/116 |
| 2015/0073247 A1 | 3/2015 | Gordon et al. | |
| 2015/0148876 A1 | 5/2015 | Glynn et al. | |
| 2016/0149292 A1 | 5/2016 | Ganton et al. | |
| 2016/0151621 A1 | 6/2016 | Maile et al. | |
| 2016/0260938 A1 * | 9/2016 | Nielsen | H01M 10/4257 |
| 2016/0308386 A1 | 10/2016 | Tang et al. | |
| 2016/0315302 A1 | 10/2016 | Aamodt et al. | |
| 2017/0172731 A1 | 6/2017 | Mattes et al. | |
| 2018/0117341 A1 | 5/2018 | Kane et al. | |
| 2018/0131047 A1 | 5/2018 | Zhao et al. | |
| 2018/0140853 A1 * | 5/2018 | Maile | A61N 1/37229 |
| 2018/0161580 A1 | 6/2018 | Demmer et al. | |
| 2018/0272138 A1 | 9/2018 | Tahmasian et al. | |
| 2019/0224077 A1 | 7/2019 | Stein et al. | |
| 2020/0079159 A1 * | 3/2020 | Destraves | B29D 30/0061 |
| 2020/0161246 A1 | 5/2020 | Blank et al. | |
| 2020/0235646 A1 | 7/2020 | Eguchi | |
| 2022/0118264 A1 | 4/2022 | Keller et al. | |
| 2022/0118265 A1 | 4/2022 | Keller et al. | |

FOREIGN PATENT DOCUMENTS

| | | | |
|---|---|---|---|
| EP | 2465575 A1 | 6/2012 | |
| EP | 3221820 A1 | 9/2017 | |
| JP | 2017-536192 A | 12/2017 | |
| WO | 2011038330 A1 | 3/2011 | |

OTHER PUBLICATIONS

International Search Report and Written Opinion received for PCT Patent Application No. PCT/US2019/062265, mailed on Mar. 6, 2020, 11 pages.

Extended European Search Report from related European Patent Application No. 24164999.5, mailed on Jun. 11, 2024 (8 pages).

First Office Action from related Chinese Patent Application No. 201980076232.6, mailed on Feb. 26, 2024 (20 pages including translation).

* cited by examiner

BIOSTIMULATOR HAVING FLEXIBLE CIRCUIT ASSEMBLY

This application is a continuation of co-pending U.S. Non-Provisional patent application Ser. No. 17/565,325, filed on Dec. 29, 2021, which is a continuation of U.S. Non-Provisional patent application Ser. No. 16/687,477, filed on Nov. 18, 2019, now issued as U.S. Pat. No. 11,247,059, which claims the benefit of priority of U.S. Provisional Patent Application No. 62/770,088, filed on Nov. 20, 2018, and these applications are incorporated herein by reference in their entirety to provide continuity of disclosure.

BACKGROUND

Field

The present disclosure relates to biostimulators. More specifically, the present disclosure relates to leadless bio-stimulators having flexible circuit assemblies.

Background Information

Cardiac pacing by an artificial pacemaker provides an electrical stimulation to the heart when its own natural pacemaker and/or conduction system fails to provide syn-chronized atrial and ventricular contractions at rates and intervals sufficient for a patient's health. Such antibradycar-dial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conduc-tors for connecting the pulse generator to electrodes in the heart. Such electrode leads typically have lengths of 50 to 70 centimeters.

A pulse generator can have electronic circuitry to control cardiac pacing by the leads. For example, the electronic circuitry may include a printed circuit board. The electronic circuitry can include an integrated circuit to control the delivery of a pacing impulse from an interior of a hermeti-cally sealed battery container to an external lead connection.

SUMMARY

Conventional pacemakers have several drawbacks, including complex connections between the leads and the pulse generator, and a risk of infection and morbidity due to the separate leads and pulse generator components. Many of the issues associated with conventional pacemakers are resolved by the development of a self-contained and self-sustainable biostimulator, or so-called leadless biostimulator. The leadless biostimulator can be attached to tissue within a dynamic environment, e.g., within a chamber of a beating heart. The attachment of the leadless biostimulator within a target anatomy, however, increases the importance of miniaturization of the device profile. Accordingly, increasing packaging efficiency of the device, including reducing an overall volume of the electronic circuitry, is desirable. Furthermore, the colocation of a battery and electronic circuitry, as well as the reduction in the overall volume of the electronic circuitry, can increase a risk of short-circuiting of the battery or circuitry by conductive residue from a manufacturing process used to fabricated the leadless biostimulator. Accordingly, isolating battery con-ductors and electronic circuitry from each other and from surrounding conductive structures can improve device reli-ability.

A biostimulator having a flexible circuit assembly, and optionally other components, that are structured and arranged to reduce the likelihood of short-circuiting, is provided. In an embodiment, the flexible circuit assembly includes a flexible substrate that has a mounting surface to carry electrical and electronic components. The flexible substrate can be folded along a fold region such that a first mounting region and a second mounting region of the mounting surface face each other. In the folded, or stacked, configuration, a feedthrough connector and an electronic component, both of which are on the mounting surface, can be enfolded by the folded flexible substrate. Accordingly, the feedthrough connector and electronic component can be protected and separated from surrounding conductive com-ponents, such as a housing or a battery.

The flexible circuit assembly can have an aperture in the fold region. The aperture can be centered on the mounting surface. For example, the aperture can be at a center of the fold region. An aperture axis of the apertures can extend in alignment with, e.g., through or over, the feedthrough con-nector. Accordingly, a feedthrough pin of a header assembly can be inserted through the aperture to connect to the feedthrough connector. The feedthrough pin can conduct electrical impulses from the flexible circuit assembly to a target tissue.

In an embodiment, battery connectors are also on the mounting surface. For example, the feedthrough connector and the battery connectors can be on the first mounting region of the mounting surface, and the electronic compo-nent, e.g., a processor, can be on the second mounting region of the mounting surface. The feedthrough connector and the battery connectors can be socket connectors having respec-tive socket axes extending parallel to each other. In an embodiment, the socket axis of the feedthrough is laterally between the socket axes of the battery connectors. Thus, the electrical pins of the feedthrough and the battery can support the flexible circuit assembly uniformly at several points when engaged with the respective connectors.

The folded flexible circuit assembly can be folded such that the flexible substrate contacts the adjacent housing and/or battery. Accordingly, the flexible substrate can sepa-rate and insulate the electrical connectors and electronic components from the surrounding structures. Alternatively, the flexible circuit assembly can be insulated from the housing and/or the battery by one or more external compo-nents. In an embodiment, an end insulator is located between the battery and the flexible circuit assembly. The end insu-lator can be a thin-walled planar dielectric film that separates the flexible circuit assembly from the battery. The end insulator can have slots to allow the battery pins to pass through the end insulator to connect to the battery connectors. In an embodiment, the biostimulator includes a wall insulator located between the housing and the flexible circuit assembly. The wall insulator can be a thin-walled tubular dielectric sleeve that extends around the flexible circuit assembly to insulate the flexible circuit assembly from the housing.

Methods of assembling the biostimulator having the flexible circuit assembly are described. The methods can have operations performed in an order according to whether the electrical connectors on the flexible substrate are socket connectors or metallized pads. In an embodiment, the methods include using circumferential welds to secure the housing to the header assembly and the battery. The welds can hermetically seal an electronics compartment containing the flexible circuit assembly. Accordingly, the biostimulator may include a moisture getter within the electronics compartment to scavenge residual moisture that could negatively impact performance of the electrical connectors or electronic components within the electronics compartment.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
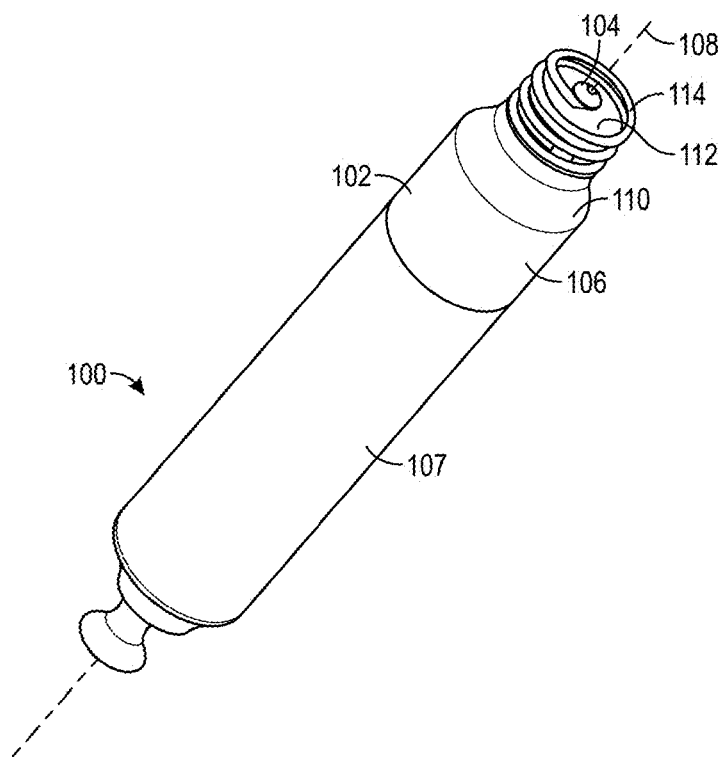
FIGS. 1A-1B are perspective and exploded views, respectively, of a biostimulator, in accordance with an embodiment.

Embodiments describe a biostimulator, e.g., a leadless cardiac pacemaker, having a flexible circuit assembly that includes a flexible substrate carrying an electronic component and an electrical connector, and an aperture in the flexible substrate to allow a feedthrough pin to pass through the flexible substrate to the electrical connector. The electronic component can include a processor to control transmission of a pacing impulse from a battery to a target tissue. The flexible circuit assembly can be folded into a stacked configuration in which the flexible substrate insulates the electronic component from surrounding structures, e.g., a housing of the biostimulator. Additional components, such as a wall insulator or an end insulator can further insulate the flexible circuit assembly from surrounding structures. The biostimulator may be used to pace cardiac tissue as described below. Alternatively, the biostimulator may be used in other applications, such as deep brain stimulation. Thus, reference to the biostimulator as being a cardiac pacemaker is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a biostimulator. Similarly, "proximal" may indicate a second direction opposite to the first direction. Such terms are provided to establish relative frames of reference, however, and are not intended to limit the use or orientation of a biostimulator to a specific configuration described in the various embodiments below.

In an aspect, a biostimulator is provided. The biostimulator includes a pacing tip for delivering a pacing impulse to a target tissue. The pacing impulse can be controlled and/or transmitted by a flexible circuit assembly having an electronic component and an electrical connector contained within an electronics compartment of the biostimulator. More particularly, the flexible circuit assembly includes an electronic component and an electrical connector on a mounting surface of a flexible substrate, which is folded in half within the electronics compartment. A first mounting region carrying the electronic component and a second mounting region carrying the electrical connector can face each other, such that the electronic component and the electrical connector are sandwiched between and enfolded by the mounting regions. The electronic component and electrical connector can be insulated from a surrounding structure, e.g., a housing of the biostimulator, by one or more of the flexible substrate, a wall insulator, or an end insulator. For example, the wall insulator can separate the flexible circuit assembly from the housing and the end insulator can separate the flexible circuit assembly from a battery to reduce a likelihood of electrical short circuiting between conductive portions of the flexible circuit assembly and either the housing or the battery.

Referring to FIG. 1A, a perspective view of a biostimulator is shown in accordance with an embodiment. A biostimulator 100 can be a leadless biostimulator, e.g., a leadless cardiac pacemaker. The biostimulator 100 can include a distal electrode 104 and a proximal electrode 106 disposed thereon. The electrodes can be integral to a housing 102, or connected to the housing, e.g., at a distance of less than several centimeters from the housing 102. The housing 102 can contain an energy source 107 to provide power to the pacing electrodes. The energy source 107 can be a battery, such as a lithium carbon monofluoride (CFx) cell, or a hybrid battery, such as a combined CFx and silver vanadium oxide (SVO/CFx) mixed-chemistry cell. Similarly, the energy source 107 can be an ultracapacitor. In an embodiment, the energy source 107 can be an energy harvesting device, such as a piezoelectric device that converts mechanical strain into electrical current or voltage. The energy source 107 can also be an ultrasound transmitter that uses ultrasound technology to transfer energy from an ultrasound subcutaneous pulse generator to a receiver-electrode implanted on an endocardial wall.

The biostimulator 100 can have a longitudinal axis 108. The longitudinal axis 108 can be an axis of symmetry, along which several biostimulator components are disposed. For example, a header assembly 110 can be mounted on a distal end of the housing 102 along the longitudinal axis 108. The header assembly 110 can include an electrical feedthrough assembly including an electrical feedthrough (not shown) and the distal electrode 104, e.g., a pacing tip. The header assembly 110 can include a helix mount 112 mounted on the electrical feedthrough assembly around the longitudinal axis 108. In an embodiment, a fixation element 114 is mounted on the helix mount 112 along the longitudinal axis 108. The assembled components of the biostimulator 100 can provide a distal region that attaches to a target tissue, e.g., via engagement of the fixation element 114 with the target tissue. The distal region can deliver a pacing impulse to the target tissue, e.g., via the distal electrode 104 that is held against the target tissue.

Figure 1B:
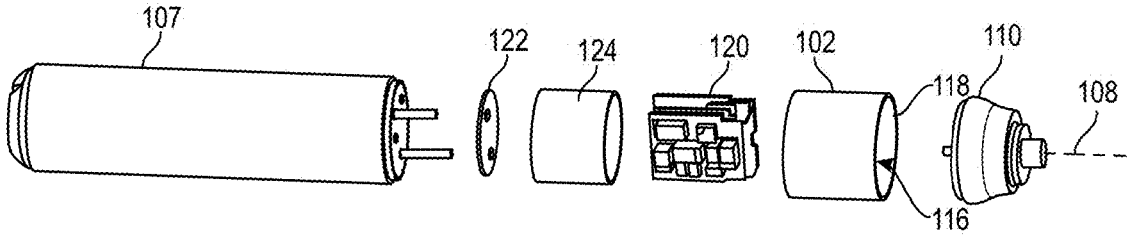

Referring to FIG. 1B, an exploded view of a biostimulator having a flexible circuit assembly is shown in accordance with an embodiment. The housing 102 can contain an electronics compartment 116. More particularly, the housing 102 can have a housing wall, e.g., a cylindrical wall, laterally surrounding the electronics compartment 116. In an embodiment, the housing wall has an inner surface 118 extending around the electronics compartment 116 on the longitudinal axis 108. The housing wall can include a conductive, biocompatible, inert, and anodically safe material such as titanium, 316L stainless steel, or other similar materials, to laterally enclose the electronics compartment 116. The electronics compartment 116 can be axially enclosed at a proximal end by the battery. More particularly, a distal surface or face of the battery can define the proximal end of the electronics compartment 116. The electronics component 116 can be axially enclosed at a distal end by the header assembly 110. More particularly, a proximal surface of the header assembly 110 can define the distal end of the electronics compartment 116. The housing 102 can be attached, e.g., welded, to the header assembly 110 and the battery 107. Accordingly, the electronics compartment 116 can be contained between the battery, the inner surface 118 of the housing 102, and the header assembly 110.

In an embodiment, a flexible circuit assembly 120 is contained within the electronics compartment 116. The flexible circuit assembly 120 can include a flexible substrate having one or more electronic components mounted on a flexible substrate. For example, the flexible circuit assembly 120 can include one or more passive electronic components, e.g., capacitors, and one or more active electronic components, e.g., processors. The electronic components can be interconnected by electrical traces, vias, or other electrical connectors. In an embodiment, the electronics assembly includes one or more electrical connectors, e.g., socket and pin connectors or metallized contact pads, to connect to the battery and the electrical feedthrough assembly. For example, the electrical connector can be a socket connector or a metallized pad to receive and/or connect to an electrode pin or a terminal pin, as described below.

The electrical connectors of the flexible circuit assembly 120 can be accidentally short-circuited to other conductive components of the biostimulator 100 such as the housing 102 or battery 107. To reduce the likelihood of such an event, the biostimulator 100 may incorporate components to electrically insulate and/or protect the flexible circuit assembly components from short-circuiting. For example, the biostimulator 100 can include an end insulator 122. The end insulator 122 can include a planar structure to form a wall between the flexible circuit assembly 120 and the energy source 107. As described below, the end insulator 122 can separate the battery, and more particularly an enclosure of the battery, from the flexible circuit assembly 120. The biostimulator 100 may also include a wall insulator 124. As described below, the wall insulator 124 can separate the flexible circuit assembly 120 from the inner surface 118 of the housing 102. It will be appreciated that the flexible substrate of the flexible circuit assembly 120 may provide sufficient insulation and separation from the housing 102 and the battery, and thus, the end insulator 122 and the wall insulator 124 are optional. The insulating components are nonetheless described as being part of the embodiments below.

Figure 2A:
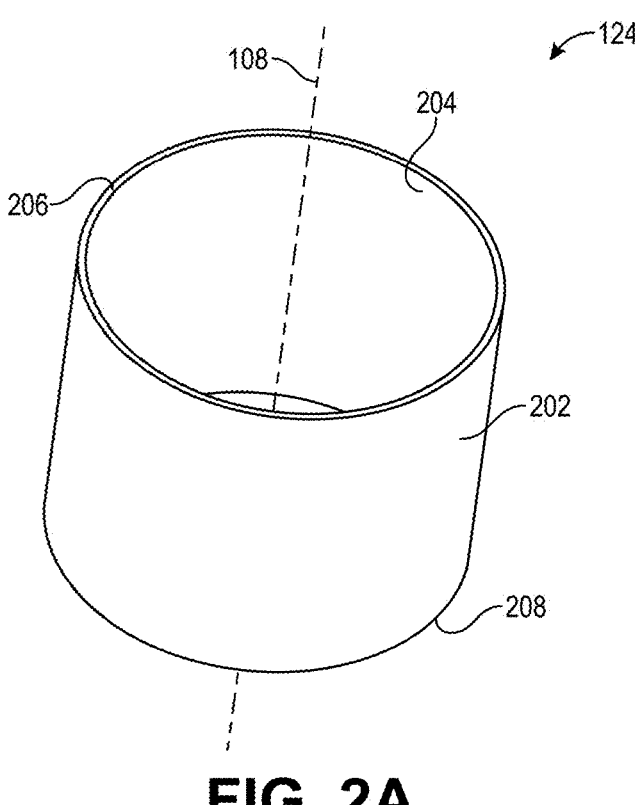
FIGS. 2A-2B are perspective views of a wall insulator, in accordance with an embodiment.

Referring to FIG. 2A, a perspective view of a wall insulator is shown in accordance with an embodiment. The flexible circuit assembly 120 can be separated from the housing 102 to reduce the likelihood of short-circuiting between the electronic components on the flexible circuit assembly 120 and the housing 102, during both manufacturing and use of the biostimulator 100. The wall insulator 124 can be a tubular component. For example, the wall insulator 124 can have the form of a cylindrical tube. The cylindrical tube can include a wall outer surface 202 and a wall interior surface 204, both of which may be cylindrical, extending between a distal wall end 206 and a proximal wall end 208. The tubular structure of the wall insulator 124 allows the insulator to be mounted over the flexible circuit assembly 120 to circumferentially enclose the flexible circuit assembly 120. More particularly, the wall insulator 124 can extend around the flexible circuit assembly 120 within the electronics compartment 116 of the biostimulator 100. Accordingly, the wall insulator 124 can separate the flexible circuit assembly 120 from the inner wall 118 of the housing 102.

In an embodiment, a cross-sectional profile of the wall insulator 124, taken along a plane extending perpendicular to the longitudinal axis 108, is circular. More particularly, a profile of the wall outer surface 202 and the wall interior surface 204 may be circular. Alternatively, the cross-sectional profile of the wall insulator 124 can be polygonal, elliptical, or another shape.

In an embodiment, the wall insulator 124 is formed from a thin dielectric film. For example, the wall insulator 124 can be a thin cylindrical insulating sleeve formed from any material having good dielectric properties (electrically insulating). As described below, the wall insulator 124 may fit within the electronics compartment 116 between the housing 102 and the flexible circuit assembly 120, and thus, it may be advantageous to form the wall insulator 124 from a material capable of forming a thin wall having tight tolerances. The wall insulator 124 may also benefit from having good hoop strength. Accordingly, the wall insulator 124 may be formed from polytetrafluoroethylene or polyimide because those materials have the desired characteristics.

Figure 2B:
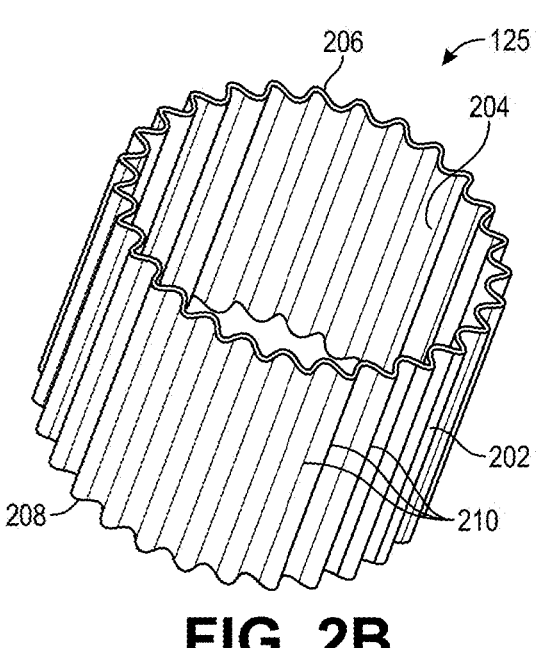

Referring to FIG. 2B, a perspective view of a wall insulator is shown in accordance with an embodiment. The wall insulator 124 may be an expandable sleeve 125. In an embodiment, the wall insulator 124 as the expandable sleeve 125 has a corrugated tubular structure. For example, the tubular structure can have several longitudinal folds 210 extending in the longitudinal direction 318 between the distal wall end 206 and the proximal wall end 208. The folds 210 or corrugations impart a non-circular profile to the wall outer surface 202 and the wall interior surface 204. More particularly, the tubular surfaces of the wall insulator 124 may define a thin wall that undulates in a circumferential direction around the longitudinal axis 108.

The longitudinal folds 210 of the wall insulator 124 allow the insulator to expand and contract radially. For example, an inward radial force applied to the wall outer surface 202 can cause an angle between the undulating surfaces to decrease, thereby reducing a diameter of the wall insulator 124. By contrast, an outward radial force applied to the wall interior surface 204 can cause the angle between the undulating surfaces to increase, thereby increasing a diameter of the wall insulator 124. The expandable/collapsible tubular structure can allow the wall insulator 124 to conform to adjacent components. For example, the wall insulator 124 can be placed within the housing 102, and may collapse such that the wall outer surface 202 contacts and fits within the inner surface 118 of the housing 102. Similarly, the wall insulator 124 can be placed over the flexible circuit assembly 120, and may expand such that the wall interior surface 204 contacts an exterior of the flexible circuit assembly 120. The wall insulator 124 may therefore adapt to the adjacent structures to provide a close fit that uses minimal space between the housing 102 and the flexible circuit assembly 120.

As mentioned above, the wall insulator 124 can be formed from any electrically insulating material. In an embodiment, the wall insulator 124 is formed from a heat-shrinkable material. For example, the wall insulator 124 may be a heat-shrinkable tube formed from a polyolefin or fluoropolymer material. In such case, heat may be applied to the wall insulator 124 to cause it to shrink onto and conform to the flexible circuit assembly 120. The heat-shrinkable tubing, when in the shrunk state, may wrap around and isolate the electronic components of the flexible circuit assembly 120 from surrounding structures, such as the housing 102.

Figure 3:
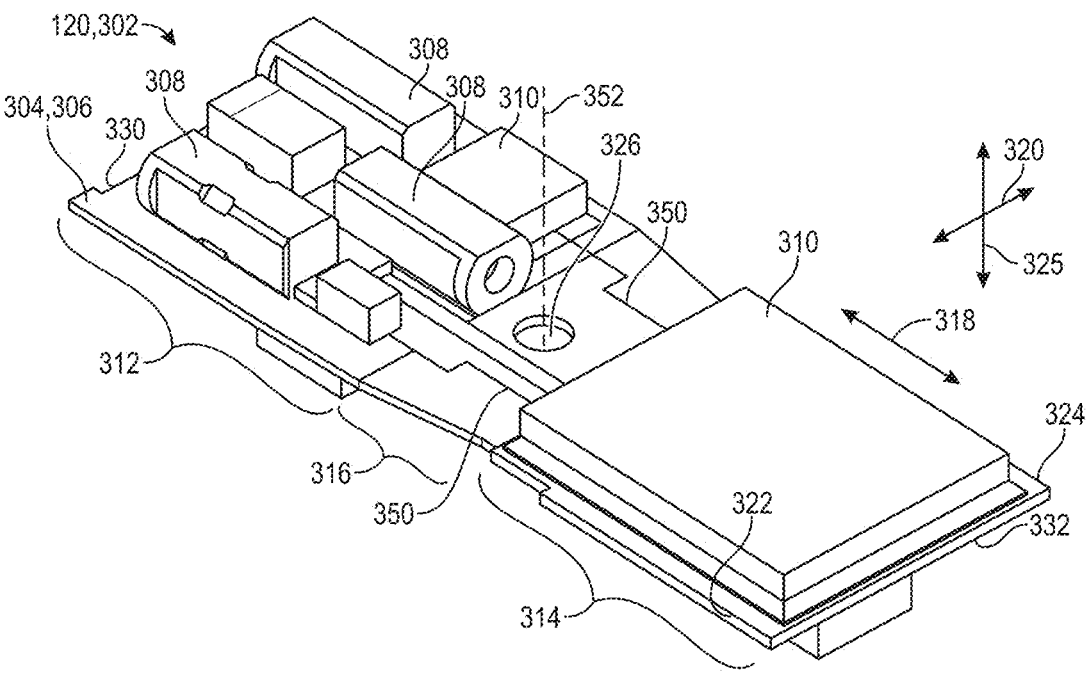
FIG. 3 is a perspective view of an inner side of a flexible circuit assembly in a flattened configuration, in accordance with an embodiment.

Referring to FIG. 3, a perspective view of an inner side of a flexible circuit assembly in a flattened configuration is shown in accordance with an embodiment. The flexible circuit assembly 120 for the biostimulator 100 can have a flattened configuration 302. In an embodiment, the flexible circuit assembly 120 includes a flexible substrate 304. For example, the flexible substrate 304 can include a flexible polymer film, such as a film including polyester, polyethylene naphthalate, polyetherimide, fluoropolymers, and combinations thereof. In an embodiment, flexible substrate 304 is a polyimide substrate that can be resiliently bent or folded.

Figure 5:
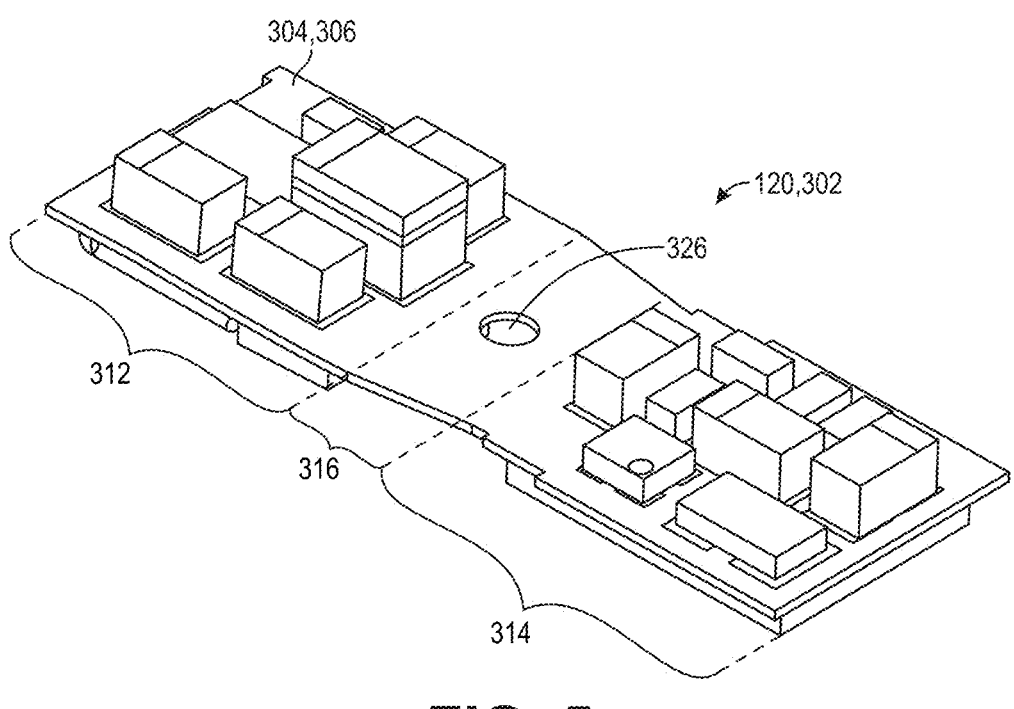
FIG. 5 is a perspective view of an outer side of a flexible circuit assembly in a flattened configuration, in accordance with an embodiment.

The flexible substrate 304 can include several mounting surfaces facing in opposite directions, e.g., a top surface (FIG. 3) and a bottom surface (FIG. 5). The top surface, which is shown in FIG. 3, may also be referred to as an inner side of the flexible circuit assembly 120 because the top surface faces an internal gap of a folded structure when the flexible circuit assembly 120 is folded from the flattened configuration 302 into a stacked configuration, as described below. In an embodiment, the mounting surfaces include a mounting surface 306 carrying one or more electrical connectors 308 and one or more electronic components 310. The mounting surface 306 can be a planar surface in the flattened configuration 302, and can have several regions designated according to their function.

In an embodiment, the mounting surface 306 of flexible substrate 304 includes a first mounting region 312 and a second mounting region 314. One or more electrical connectors 308 and/or electronic components 310 can be mounted on first mounting region 312. Similarly, one or more electrical connectors 308 and/or electronic components 310 can be mounted on second mounting region 314. In an embodiment, only one of the mounting regions carries electrical connector(s) 308.

The mounting surface 306 can include a fold region 316 between the first mounting region 312 and the second mounting region 314. For example, each mounting region can have a region boundary defined by longitudinal boundaries separated in a longitudinal direction 318, and lateral boundaries separated in a lateral direction 320. The fold region 316 can be a segment of the flexible substrate 304 extending across the mounting surface 306 in the lateral direction 320 from a first lateral edge 322 of the flexible substrate 304 to a second lateral edge 324 of the flexible substrate 304. The flexible substrate 304 is configured to fold along the fold region 316 into a stacked configuration (FIG. 7) such that the first mounting region 312 of the inner surface faces the second mounting region 314 of the inner surface in a transverse direction 325 orthogonal to the longitudinal direction 318 and the lateral direction 320.

In an embodiment, one or more electrical traces 350 extend over the fold region 316. More particularly, the electrical traces 350 can extend from the first mounting region 312 to the second mounting region 314 across the fold region 316. The electrical traces 350 can be disposed on, or embedded within, the flexible substrate 304. The electrical traces 350 can electrically connect a first component, e.g., a socket connector, mounted on the first mounting region 312 to a second component, e.g., a processor, mounted on the second mounting region 314. Accordingly, the electrical traces 350 can fulfill an electrical communication function.

The electrical traces 350 may also fulfill a mechanical function. In an embodiment, the electrical traces 350 act as strain reliefs to distribute stress evenly over the fold region 316. The electrical traces 350 can have a thickness and/or width to prevent kinking in the fold region 316. Furthermore, the electrical traces 350 may be formed from a ductile material that resists kinking. For example, the electrical traces 350 can be copper alloy traces having predetermined dimensions and traces per inch density, which are embedded in flexible substrate 304 within the fold region 316 such that, when the flexible circuit assembly is folded into a stacked configuration (FIG. 7), the fold region 316 extends along an arcuate path, e.g., a smooth curve, rather than kinking or bending abruptly.

In an embodiment, the flexible substrate 304 includes an aperture 326 extending through the flexible substrate 304. More particularly, the aperture 326 can be a hole or a slot extending from the inner side of the flexible substrate 304 to the outer side on an opposite side of the flexible substrate 304. The aperture 326 can be in the fold region 316, and can have an aperture axis 352. The aperture axis 352 may be defined with respect to an edge of the aperture 326. For example, an aperture plane may contain the edge that extends around the aperture 326, and the aperture axis 352 may extend perpendicular to the aperture plane. Accordingly, the aperture axis 352 may be parallel to the transverse direction 325 when the flexible circuit assembly 120 is in the flattened configuration 302, and by contrast, the aperture axis 352 may be parallel to the longitudinal direction 108 when the flexible circuit assembly 120 is in the stacked configuration. In the stacked configuration, the aperture axis 352 can be parallel to the longitudinal axis 108, as described below.

In an embodiment, the aperture 326 can be centered on the mounting surface 306. For example, the fold region 316 can be spaced equally between a first longitudinal edge 330 and a second longitudinal edge 332 of flexible substrate 304. Accordingly, the aperture 326 in the fold region 316 can be longitudinally centered between the first longitudinal edge 330 and the second longitudinal edge 332. Similarly, the aperture 326 in the fold region 316 can be laterally centered between the first lateral edge 322 and the second lateral edge 324. Thus, the aperture 326 can be at a center of the mounting surface 306.

Figure 4:
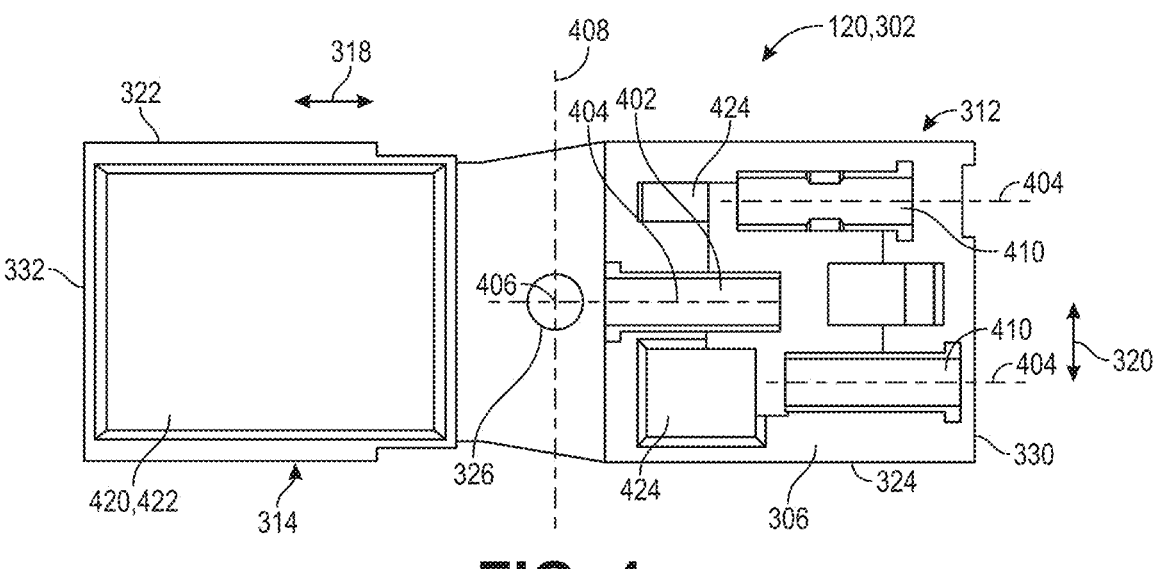
FIG. 4 is a plan view of an inner side of a flexible circuit assembly, in accordance with an embodiment.
Figure 13:
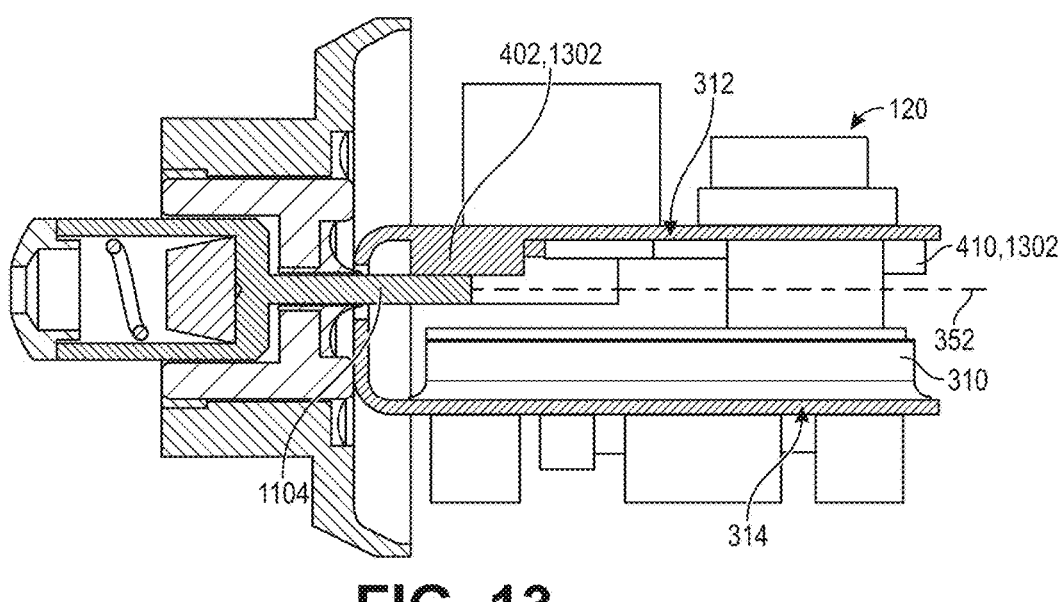
FIG. 13 is a cross-sectional view of a header assembly connected to a flexible circuit assembly, in accordance with an embodiment.
Figure 14:
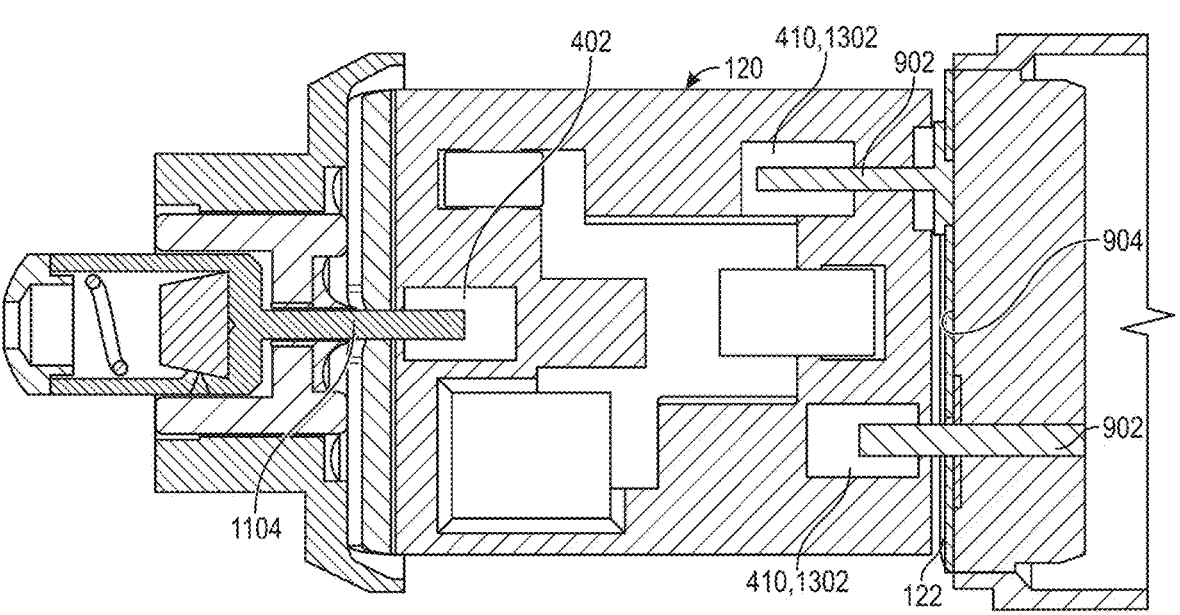
FIG. 14 is a cross-sectional view of a header assembly and a battery connected to a flexible circuit assembly, in accordance with an embodiment.
Figure 15:
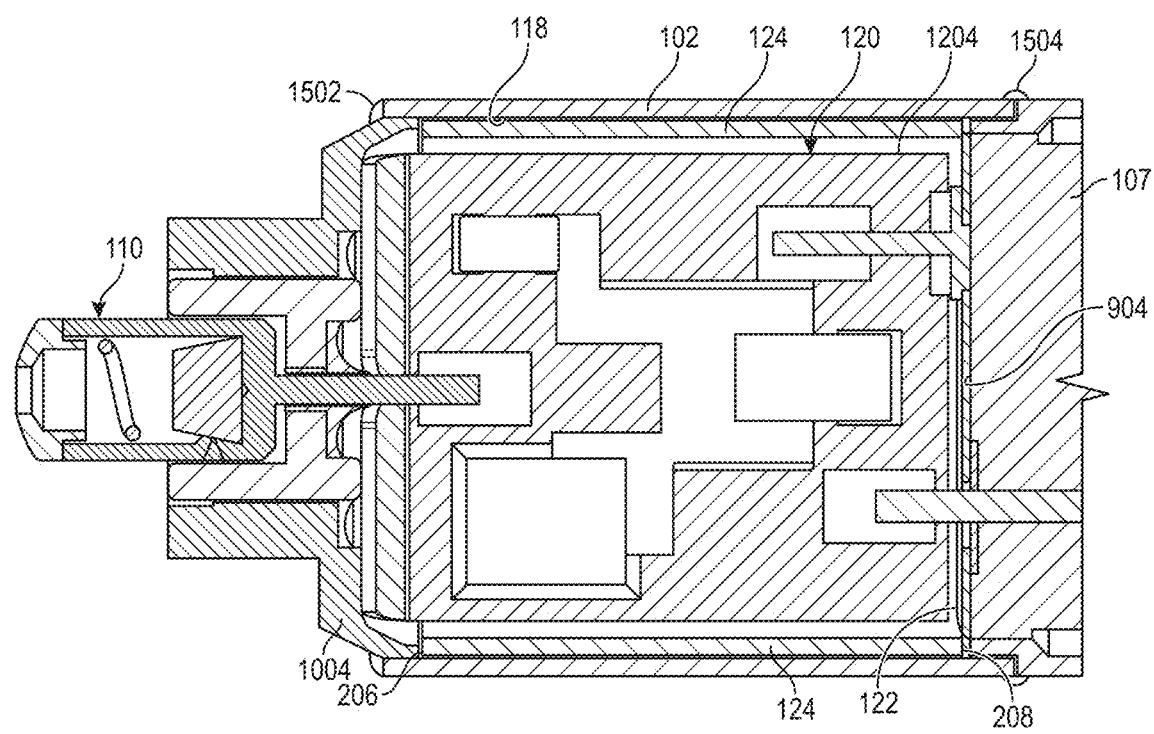
FIG. 15 is a cross-sectional view of an electronics compartment of a biostimulator containing a wall insulator and a flexible circuit assembly, in accordance with an embodiment.

Referring to FIG. 4, a plan view of an inner side of a flexible circuit assembly is shown in accordance with an embodiment. The electrical connectors 308 on the mounting surface 306 can include a feedthrough connector 402 mounted on the first mounting region 312. The feedthrough connector 402 can be one of several types of electrical connectors 308. For example, the feedthrough connector 402 can be a socket connector (FIGS. 3-7 and 10-12) or a metallized pad (FIGS. 13-15). The feedthrough connector 402 can be configured to receive an electrical pin from another component of the biostimulator 100. For example, the feedthrough connector 402 can receive and/or attach to a feedthrough pin of the header assembly 110 that transmits a pacing impulse from the flexible circuit assembly 120 to the pacing tip of the biostimulator 100.

In an embodiment, the feedthrough connector 402 is a socket connector and has a socket axis 404 passing through a lumen of the socket connector. The socket axis 404 can extend in the longitudinal direction 318. In an embodiment, the socket axis 404 is laterally aligned with a center 406 of the mounting surface 306. Accordingly, the socket axis 404 can be transversely aligned with the aperture 326.

As described above, the aperture 326 can be centered on the mounting surface 306. The center 406 can be aligned with the socket axis 404 that is equidistantly spaced between the first lateral edge 322 and the second lateral edge 324. Similarly, the center 406 can be aligned with a midline 408 of the mounting surface 306, which extends orthogonal to the socket axis 404. The midline 408 can be equidistantly spaced between the first longitudinal edge 330 and the second longitudinal edge 332 of the flexible substrate 304.

The flexible circuit assembly 120 can include several electrical connectors 308 on the mounting surface 306. For example, one or more battery connectors 410 can be on the mounting surface 306. The battery connectors 410 can be one of several types of electrical connectors 308. For example, the battery connectors 410 can be socket connectors (FIGS. 3-7 and 10-12) or metallized pads (FIGS. 13-15). The battery connectors 410 may be configured to receive and/or attach to electrical pins of another component of the biostimulator 100. For example, battery connectors 410 can receive battery pins of the energy source 107 to transmit power from the battery to the flexible circuit assembly 120. The battery pins can be a positive terminal post and a negative terminal post of the battery. Accordingly, electrical power can be input to the flexible circuit assembly 120 via the battery connectors 410, and electrical power can be output from the flexible circuit assembly 120 via the feedthrough connector 402.

Each battery connector 410 can be a socket connector having a respective socket axis 404. The respective socket axes 404 of the battery connectors 410 can extend parallel to the socket axis 404 of the feedthrough connector 402. In an embodiment, the socket axes 404 of the flexible circuit assembly 120 extend in the longitudinal direction 318 of the biostimulator 100. For example, the socket axes can be parallel to the longitudinal axis 108 when the flexible circuit assembly 120 is contained within the electronics compartment 116 of the housing 102. Notably, the socket axes 404 may also be parallel to the aperture axis 352 in such a configuration. Accordingly, as described further below, when the flexible circuit assembly 120 is folded about the fold region 316 to mount the flexible circuit assembly 120 within the electronics compartment 116, the reference geometry of the socket axes 404 extend longitudinally through the fold region 316 of the mounting surface 306. More particularly, the socket axes 404 can extend parallel to mounting surface 306 over the first and second mounting regions, and orthogonal to the mounting surface 306 at the locations where the axes intersect the fold region 316.

The electrical connectors 308 of the flexible circuit assembly 120 may be located to stably support the flexible circuit assembly 120 on the electrical pins that the socket connectors receive. In an embodiment, the external pins, e.g., the feedthrough pin and the battery pins, can be evenly loaded by the electrical connectors 308 on the mounting surface 306. For example, the socket axis 404 of the feedthrough connector 402 can be located between the socket axes 404 of the battery connectors 410. More particularly, the socket axis 404 of the feedthrough connector 402 may be laterally between, relative to the lateral direction 320, the socket axes of the battery connectors 410. In an embodiment, the socket axis 404 of the feedthrough connector 402 is equidistantly spaced between the socket axes 404 of the battery connectors 410. Accordingly, the mechanical connections formed between the electrical connectors 308 of the flexible circuit assembly 120 and the external biostimulator components can be symmetrically located across the first mounting region 312.

Still referring to FIG. 4, in addition to having several electrical connectors 308, flexible substrate 304 can carry one or more electronic components 310 on the mounting surface 306. In an embodiment, one or more of the electronic components 310 is on the second mounting region 314 of the mounting surface 306. For example, the electronic component 310 on the second mounting region 314 can include an active electronic component 420, such as a semiconductor device. The electronic component 310 on the second mounting region 314 can include one or more processors 422. More particularly, the electronic component 310 can include an integrated circuit, such as an application-specific integrated circuit, having microprocessors and/or memory blocks designed to run in the biostimulator 100 to provide cardiac pacing. In an embodiment, the one or more processors 422 are configured to execute instructions stored in a non-transitory computer readable media to cause the biostimulator 100 to perform various operations, including but not limited to generating and transmitting the pacing impulse to the target tissue.

In addition to active components 420, flexible circuit assembly 120 can include one or more passive electronic components 424 mounted on the mounting surface 306. For example, the passive electronic components 424 can include one or more capacitors. The capacitors can be polymer or ceramic capacitors, by way of example.

In an embodiment, a shear stress applied to the electronic components 310 and/or electrical connectors 308 mounted on the mounting surface 306 can be mitigated by an epoxy underfill. More particularly, the epoxy underfill can be disposed between the mounting surface 306 and the electrical/electronic components 310 during manufacturing. The epoxy underfill can be a layer of epoxy adhesive that is flowed between the electrical/electronic components 310 and the mounting surface 306 after the electrical/electronic components 310 are mounted on the mounting surface 306. For example, surface mount technology, e.g., reflowed solder balls, can be used to electrically and/or physically connect the components to electrical contacts on the mounting surface 306, and a gap can remain between the components and the surface after component attachment. The epoxy adhesive can be flowed into the gap to further stabilize and secure the components on the mounting surface 306. In an embodiment, the underfill layer can have a thickness of 0.008 inch to 0.1 inch, e.g., 0.010 inch.

Referring to FIG. 5, a perspective view of an outer side of a flexible circuit assembly in a flattened configuration is shown in accordance with an embodiment. In the flattened configuration 302, a second surface of the flexible substrate 304 can have a respective mounting surface 306 divided into regions as described above. For example, the mounting surface 306 can have the first mounting region 312 and the second mounting region 314. The second surface may be referred to as the outer side of the flexible circuit assembly 120 because the second surface may face outwardly toward the housing 102 when the flexible substrate 304 is folded from the flattened configuration 302 into the stacked configuration as described below.

Figure 6:
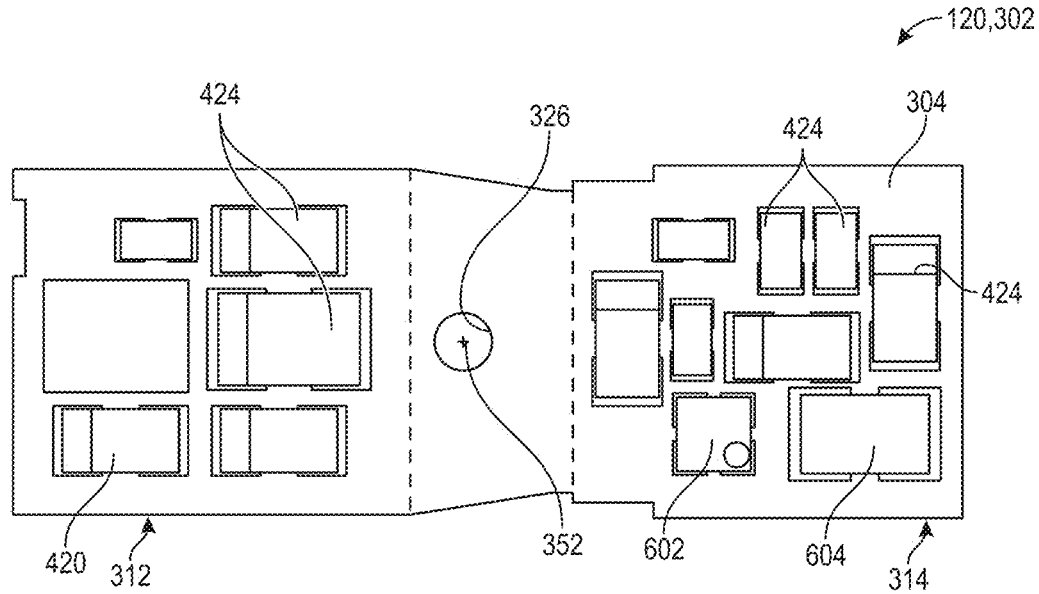
FIG. 6 is a plan view of an outer side of a flexible circuit assembly, in accordance with an embodiment.

Referring to FIG. 6, a plan view of an outer side of a flexible circuit assembly is shown in accordance with an embodiment. The mounting regions of the bottom surface can carry one or more electronic components 310, which can be active components 420 or passive components 424. For example, the electronic components 310 can include diodes, transistors, capacitors, etc. In an embodiment, the mounting regions of the outer side carry one or more sensors 602. The sensor 602(s) can detect temperature, acceleration, etc. For example, a micro electromechanical system (MEMS) sensor can be mounted on the flexible substrate 304. The MEMS sensor can be a giant magnetoresistance (GMR) sensor, by way of example. Similarly, an electronic oscillator circuit 604 can be mounted on the flexible substrate 304. It will be appreciated that the electronic components 310 described above are provided by way of example, and that other electronic components 310 may be mounted on flexible substrate 304. More particularly, surface-mount technology can be used to produce flexible circuit assembly 120 having components mounted or placed directly on the flexible substrate 304. Electrical connections between the individual components may be made using traces, electrical vias, pins, contacts, etc. For example, as described above, the electrical traces 350 can extend over the fold region 316 from components on the first mounting region 312 to components on the second mounting region 314. The electrical traces 350 can be exposed or buried, e.g., laminated. Accordingly, a two-sided flexible circuit assembly 120 having a centrally-located aperture 326 can be provided for use in the biostimulator 100.

Figure 7:
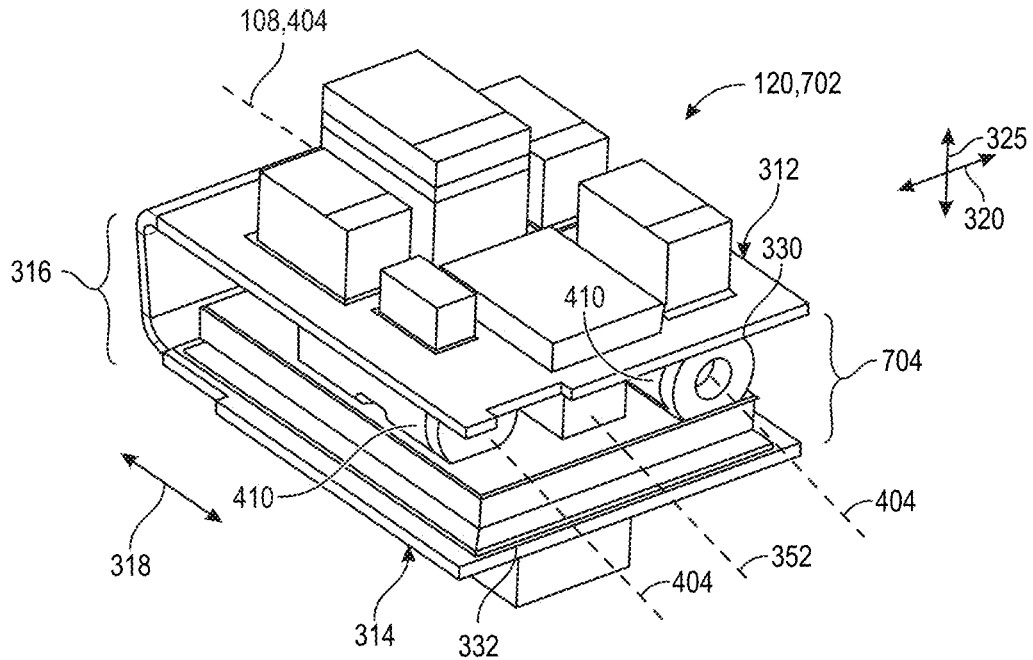
FIG. 7 is a is a perspective view of a flexible circuit assembly in a stacked configuration, in accordance with an embodiment.
Figure 11:
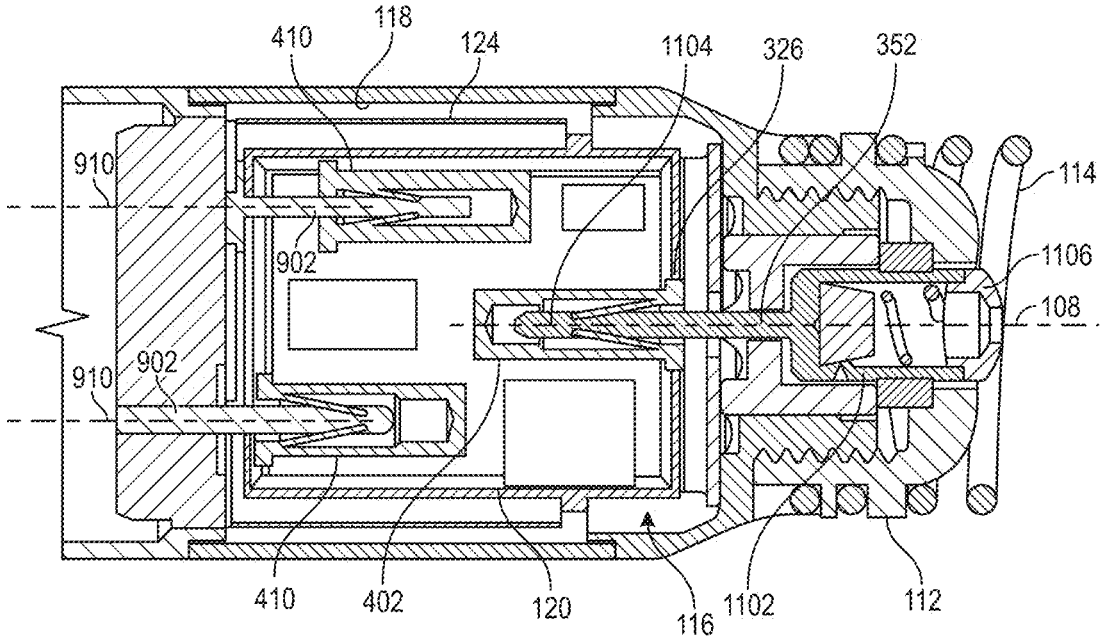
FIG. 11 is a cross-section electronics compartment of a biostimulator having a flexible circuit assembly, in accordance with an embodiment.

Referring to FIG. 7, a perspective view of a flexible circuit assembly in a stacked configuration is shown in accordance with an embodiment. The flexible circuit assembly 120 can be folded along the fold region 316 into a stacked configuration 702. In the stacked configuration 702, the socket axis 404 of the feedthrough connector 402 can extend through the aperture 326 in the longitudinal direction 318 (FIG. 11). Similarly, the aperture axis 352 can extend between the first mounting region 312 and the second mounting region 314 in the stacked configuration 702. For example, the socket axis 404 can extend through the aperture 326 parallel to the longitudinal axis 108, and the aperture axis 352 can extend through the aperture 326 in alignment with the feedthrough connector 402. More particularly, the aperture axis 352 can extend through a pin port of the socket connector that receives an external pin. Similarly, the socket axes 404 of the battery connectors 410 can extend in the longitudinal direction 318 opposite to the socket axis 404 of the feedthrough connector 402 to emerge from a protective gap 704 defined between the first longitudinal edge 330 and the second longitudinal edge 332. The aperture axis 352 can extend between the mounting regions to emerge from the protective gap 704 laterally between the socket axes of the battery connectors 410.

The protective gap 704 can be a space enfolded by the flexible substrate between the first mounting region 312 and the second mounting region 314. In the stacked configuration 702, the first mounting region 312 faces the second mounting region 314 across the protective gap 704. Accordingly, the electrical connectors 308 and/or electronic components 310 mounted on the inner side of the flexible circuit assembly 120 are contained within the protective gap 704 in the stacked configuration 702. For example, the feedthrough connector 402 and the electronic component 310 can be stacked on each other, and thus, are in the stacked configuration 702. The flexible substrate 304 can wrap around the electronic components 310 and the electrical connectors 308. The components are therefore enclosed within the protective gap 704, and thus, a likelihood that conductive debris will form a short-circuit between the components and a location outside of the protective gap 704 is reduced. The likelihood can be further reduced by closing off the ends of the protective gap 704, e.g., where the protective gap 704 opens to the surrounding environment in the longitudinal direction 318 or the lateral direction 320.

Figure 8:
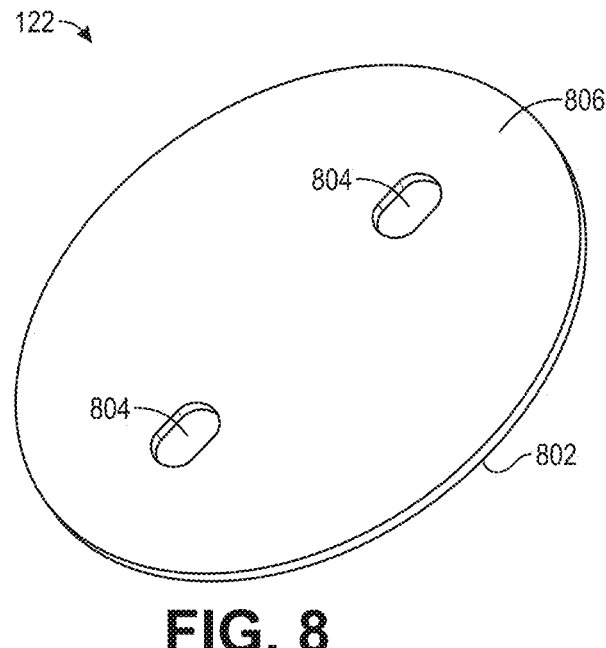
FIG. 8 is a perspective view of an end insulator of a biostimulator, in accordance with an embodiment.

Referring to FIG. 8, a perspective view of an end insulator of a biostimulator is shown in accordance with an embodiment. The end insulator 122 can be placed between the openings of the protective gap 704 and the surrounding environment. In an embodiment, the end insulator 122 is planar, e.g., has a flat distal end face 806 and a flat proximal end face (hidden from view). More particularly, the end insulator 122 can be a thin, flat, disc-shaped insulator. The end insulator 122 can include a thin dielectric film formed from a dielectric material, e.g., polyimide. The end insulator 122 may include an outer edge 802 defining a profile of the end insulator 122. For example, the profile of the end insulator 122 can be circular, as shown in FIG. 8. Alternatively, the end insulator 122 can have a polygonal, elliptical, or other profile shape.

In an embodiment, the end insulator 122 includes one or more slots 804 extending through the thin wall of the insulator. For example, the end insulator 122 can include several slots 804, each having a respective size and profile. As shown, the several slots 804 can include a pair of slots 804, each having a circular profile. The slots may be elliptical, polygonal, etc. A dimension of the profiles, e.g., a diameter of the circles, however, may differ. For example a first slot 804 of the end insulator 122 may have a larger diameter than a second slot 804 of the end insulator 122. Alternatively, the slots 804 may have a same size and shape. For example, the slots 804 of the end insulator 122 may both be elliptical and have a same length and width.

Figure 9:
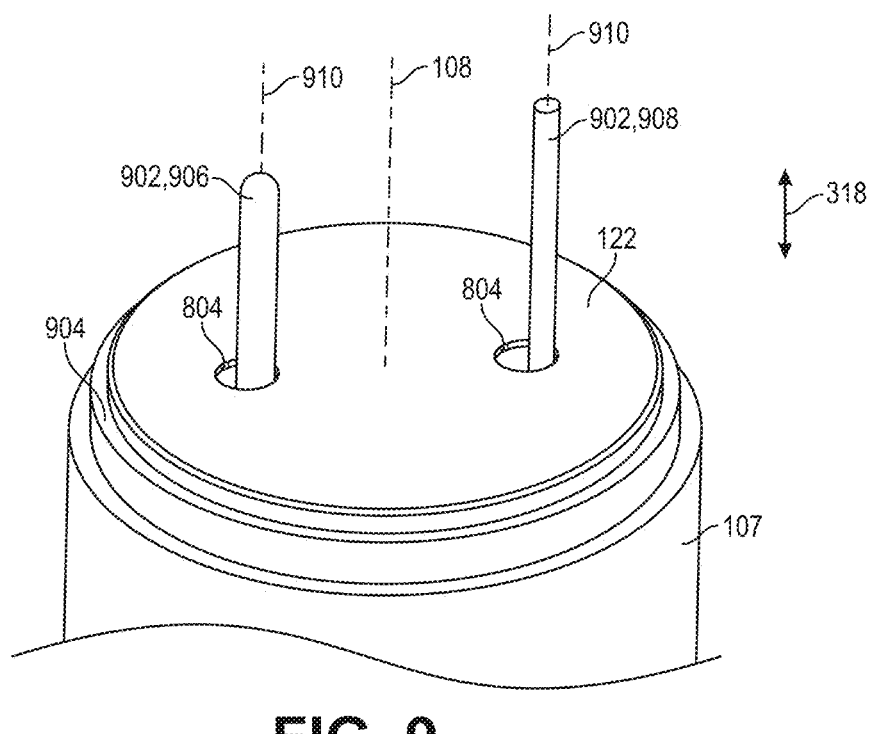
FIG. 9 is a perspective view of battery pins extending through an end insulator of a biostimulator, in accordance with an embodiment.

Referring to FIG. 9, a perspective view of battery pins extending through an end insulator of a biostimulator is shown in accordance with an embodiment. The end insulator 122 may be configured to cover a face of the energy source 107 while allowing the terminal posts of the battery to pass through the end insulator 122 into electrical contact with the electrical connectors 308 of the flexible circuit assembly 120. In an embodiment, the battery includes one or more battery pins 902, which can be the positive and negative terminal posts of the battery. The battery pins 902 can extend from a distal face 904 of the battery in the longitudinal direction 318, e.g., parallel to the longitudinal axis 108. More particularly, the battery pins 902 can have respective pin axes 910, and the pin axes 910 can extend parallel to the aperture axis 352 when the flexible circuit assembly 120 is in the stacked configuration 702. During assembly of the biostimulator 100, the battery pins 902 can be inserted through respective slots 804 of the end insulator 122.

Accordingly, the end insulator 122 can be laid on the distal face 904 of the battery to insulate the distal face 904 and the active terminal pin from conductive debris that is on an opposite side of the end insulator 122, e.g., toward the distal tips of the battery pins 902.

In an embodiment, the battery pins 902 include a positive pin 906 and a negative pin 908. Each of the battery pin 902 outer diameter sizes and lengths can be varied to allow for a single, correct placement of the pins into their respective battery connectors 410 on the flexible circuit assembly 120. These differently sized battery pins 902 can prevent the incorrect insertion into the battery connectors 410, which could cause latent and catastrophic failures within the flexible circuit assembly 120. For example, the positive pin 906 can have a larger diameter than the negative pin 908, and accordingly, the battery connector 410 that receives the negative pin 908 may have a socket that includes a socket port that is too small to receive the positive pin 906. Accordingly, the pin sizes ensure that the battery will be correctly oriented with respect to the flexible circuit assembly 120 when the components are assembled.

In addition to controlling pin orientation, the pin size can preferentially direct force to one of the battery pins 902. For example, the positive pin 906 may interface with the glass-to-metal feedthrough of the battery, and thus, it may be advantageous to steer deflection forces toward the negative pin 908, which interfaces with the battery metal header. More particularly, the glass-to-metal feedthrough may be more fragile than the battery metal header, and thus, it may be advantageous to apply strain to the negative pin 908, which transmits forces to the battery metal header, rather than to the positive pin 906, which transmits forces to the glass-to-metal feedthrough. For example, off-axis assembly forces, e.g., generated during manual assembly, can be directed or focused on the negative pin 908 to protect the positive pin 906 and glass-to-metal feedthrough seal. This preferential direction of the off-axis assembly forces can occur for several reasons. First, the negative pin 908 may be longer than the positive pin 906, and thus, the negative pin 908 may be contacted by an assembler or an external component before the positive pin 906 is contacted. Second, negative pin 908 may be narrower and/or longer than the positive pin 906, and thus, may deflect more readily under the off-axis assembly forces. Accordingly, deflection and stresses can be directed toward the negative pin 908 to reduce the likelihood of damage to the glass-metal seal.

Figure 10:
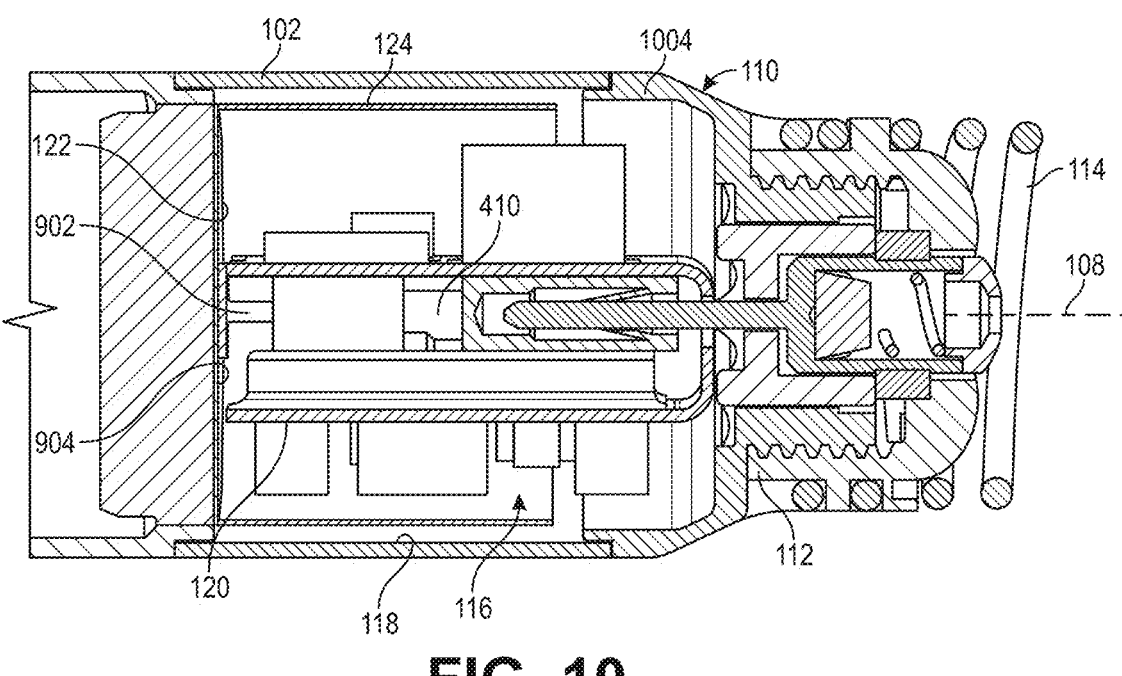
FIG. 10 is a cross-sectional view of an electronics compartment of a biostimulator having a flexible circuit assembly, in accordance with an embodiment.

Referring to FIG. 10, a cutaway view of an electronics compartment of a biostimulator having a flexible circuit assembly is shown in accordance with an embodiment. Each of the battery pins 902 of the battery can be connected to and/or mounted on or inside of respective battery connectors 410. For example, in the case of socket connectors, each battery pin 902 can be inserted through respective slots 804 in the end insulator 122, and can extend through the slot 804 into the socket of the respective battery connector 410. Similarly, in the case of metallized pads, each battery pin 902 can extend through respective slots 804 in the end insulator 122, and can attach to metallized pads of the flexible circuit assembly 120. As such, in the assembled state, the end insulator 122 can be between the distal face 904 of the battery and the flexible circuit assembly 120 when the battery pins 902 are connected to respective battery connectors 410. Accordingly, the flexible circuit assembly 120 can include several battery connectors 410 mounted on or attached to respective battery pins 902 of the battery, and the conductive components of the flexible circuit assembly 120 can be isolated from the distal face 904 of the battery by the end insulator 122.

Still referring to FIG. 10, the housing 102 can be mounted over the wall insulator 124 and onto the battery to contain the flexible circuit assembly 120 within the electronics compartment 116. More particularly, the inner surface 118 of the housing 102 can extend around the flexible circuit assembly 120 to laterally surround the flexible circuit assembly 120. In an embodiment, the header assembly 110 can be mounted on the housing 102 to contain the electronics compartment 116 within the biostimulator 100.

The header assembly 110 can include several subcomponents. For example, the header assembly 110 may include a flange 1004 having a mounting wall to receive a helix mount 112. In an embodiment, the flange 1004 is formed from titanium. The flange 1004 can be mounted on the housing 102 and connected to the housing 102 by a hermetic seal, e.g., by a weld. For example, the hermetic weld can be formed circumferentially around a seam between a proximal end of the flange 1004 and a distal end of the housing 102. In an embodiment, the helix mount 112 is mounted on the flange 1004 by a threaded connection. The flange 1004 can have an external thread that mates with an internal thread of the helix mount 112. Accordingly, the helix mount 112 can be screwed onto the mounting wall of the flange 1004. Alternatively, the helix mount 112 can be press fit onto the mounting wall, the helix mount 112 can be bonded to the mounting wall by a thermal or adhesive bond, or the helix mount 112 and the electrical feedthrough assembly can be joined in another manner, such as swaging. Accordingly, the electronics compartment 116 can be contained between the battery, the inner surface 118 of the housing 102, and the header assembly 110.

In an embodiment, the header assembly 110 includes the fixation element 114, e.g., a helix. The helix can extend distally from the helix mount 112 about the longitudinal axis 108. For example, the helix can revolve about the longitudinal axis 108. The helix can include a spiral wire, formed by coiling or cut from a wall of a tubing, which extends in a rotational direction around the longitudinal axis 108. For example, the helix can revolve in a right-handed direction about the longitudinal axis 108.

The helix can be suitable for attaching the biostimulator 100 to tissue, such as heart tissue. For example, in the case of a right-handed spiral direction, the biostimulator 100 can be advanced into contact with a target tissue, and the biostimulator 100 can then be rotated in the right-handed direction to screw the helix into the tissue.

Referring to FIG. 11, a cross-sectional view of a biostimulator having a flexible circuit is shown in accordance with an embodiment. The header assembly 110 can include a feedthrough 1102 to transmit the pacing impulses from the flexible circuit assembly 120 into the target tissue. For example, the feedthrough 1102 can have a feedthrough pin 1104. The feedthrough pin 1104 can extend proximally through the flange 1004 into the electronics compartment 116 to engage the feedthrough connector 402. More particularly, the feedthrough pin 1104 can be inserted through the aperture 326 in the fold region 316 of the flexible substrate 304 and into the feedthrough connector 402. Accordingly, the feedthrough pin 1104 can be mechanically and electrically connected to the feedthrough connector 402 between the first mounting region 312 and the second mounting region 314 of the mounting surface 306.

The feedthrough 1102 can also include an electrode tip 1106, which can be electrically continuous with the feedthrough pin 1104. Accordingly, when the fixation element 114 is engaged with the target tissue, the electrode tip 1106 can be held against the tissue, and thus, the pacing impulse can be delivered from the feedthrough connector 402 into the feedthrough pin 1104 and through the electrode tip 1106 into the target tissue.

As the flexible circuit assembly 120 can provide power to the feedthrough 1102 via feedthrough connector 402, so can the flexible circuit assembly 120 receive power from the battery through the battery connectors 410. More particularly, the battery pins 902 can extend through the slots 804 of the end insulator 122 into the electronics compartment 116. The battery pins 902 can have respective pin axes 910, and each of the pin axes 910 can be parallel to the aperture axis 352. The battery pins 902 can mechanically and electrically connect to the battery connectors 410. Accordingly, the electrical connectors 308 of the flexible circuit assembly 120 can form secure and stable connections to the battery pins 902 and the feedthrough pin 1104 to allow electrical transmission of power with a reduced likelihood of short-circuiting the electrical connectors 308 to another component of the biostimulator 100.

Figure 12:
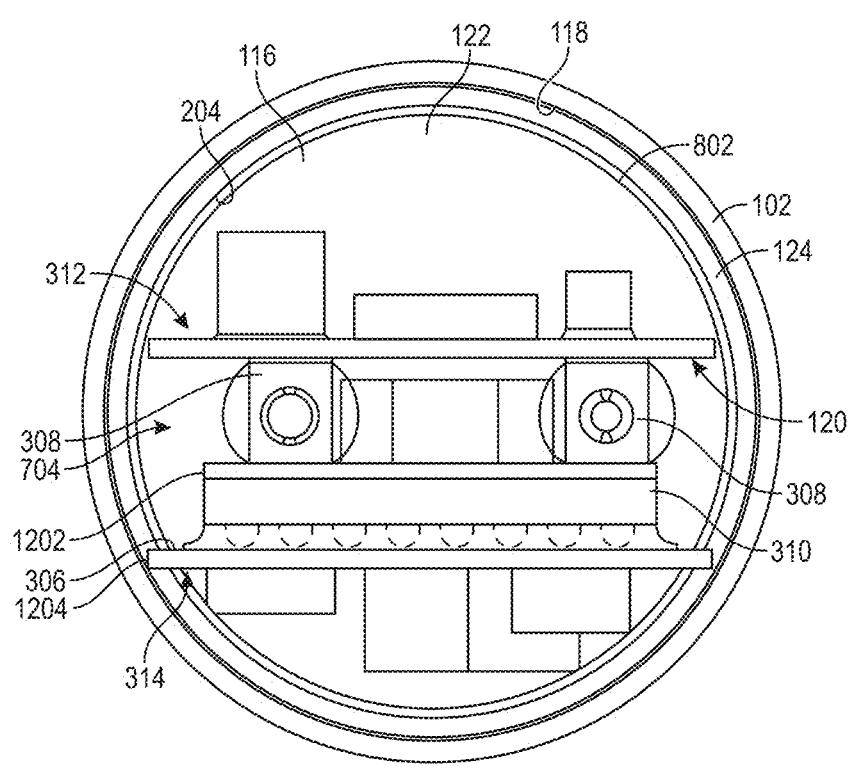
FIG. 12 is a cross-sectional view of a biostimulator having a flexible circuit assembly, in accordance with an embodiment.

Referring to FIG. 12, a cross-sectional view of a biostimulator having a flexible circuit assembly is shown in accordance with an embodiment. In addition to the protective function of the folded flexible circuit assembly 120, the stacked configuration 702 allows the electronics compartment 116 to be efficiently occupied by the circuit components. For example, stacking the electrical connectors 308 and the electronic components 310 allows more circuitry per unit length in the longitudinal direction 318 within the electronics compartment 116. In an embodiment, the stacked flexible circuit assembly 120 can be circumferentially enclosed by the wall insulator 124 that can electrically isolate the assembly from the inner surface 118 of the housing 102. As shown, the end insulator 122 can have the outer edge 802 having a circular profile, and the inner surface 118 of the housing 102 and/or the interior surface 204 of the wall insulator 124 can have the same circular profile. The circular profile is provided by way of example only, and the inner surface 118 and/or the outer edge 802 may have an alternative profile, such as a polygonal or elliptical profile. The profiles of the inner surface 118 (or interior surface 204) and the outer edge 802 can be similarly sized, e.g., can have a same diameter within a tolerance of +/−10%, to allow for the wall insulator 124, and the end insulator 122 to fully encompass the flexible circuit assembly 120 and its components while still fitting inside the housing 102.

The biostimulator 100 can include components to further insulate and protect the flexible circuit assembly components. In an embodiment, the biostimulator 100 includes a foam tape 1202 between the electrical connector(s) 308 and the electronic component 310, which are mounted within the protective gap 704. For example, the foam tape 1202 can be a strip of tape having a perimeter that is the same size as a perimeter of the first mounting region 312 and/or the second mounting region 314. The foam tape 1202 can be single-sided or double-sided tape, and can be mounted over the first mounting region 312 or the second mounting region 314 when the flexible circuit assembly 120 is in the flattened configuration 302. When the flexible circuit assembly 120 is folded into the stacked configuration 702, a first side of the tape can face the first mounting region 312 and a second side of the tape can face the second mounting region 314. The foam tape 1202 can adhere to the electronic components 310 and/or the electrical connectors 308 on the interior side of the folded substrate to retain the flexible circuit assembly 120 in the folded configuration until the socket connectors are mounted on the plug connectors of the biostimulator 100. Furthermore, the foam tape 1202 can be formed from an insulating foam material, and thus, can reduce a likelihood of electrical contact between electrical components on the first mounting region 312 and electrical components on the second mounting region 314.

In an embodiment, the flexible substrate 304 of the flexible circuit assembly 120 insulates and stabilizes the electronic components 310 and the electrical connectors 308 relative to the housing 102. As described above, the flexible substrate 304 can be a thin dielectric film, e.g., a strip of flexible polyimide. The flexible substrate 304 can have a peripheral edge 1204 that extends around the mounting surface 306 of the flexible circuit assembly 120, e.g., along the lateral and longitudinal edges of the mounting regions and the fold region 316. More particularly, the peripheral edge 1204 can include the lateral and longitudinal edges of the mounting regions and the fold region 316. At least a portion of the peripheral edge 1204 can be in contact with the wall insulator 124 along the inside of the housing 102. For example, when the flexible circuit assembly 120 is in the stacked configuration 702 and enclosed within the electronics compartment 116, the mounting regions can move away from each other, e.g., if the foam tape 1202 loses adherence to one side of the substrate, and as the substrate halves move outward, the peripheral edge 1204 can contact the interior surface of the wall insulator 124. The wall insulator can constrain the outward movement of the flexible substrate 304, and a portion of the peripheral edge 1204, e.g., the first lateral edge 322 or the second lateral edge 324, can contact the wall insulator 124, on an opposite side of the insulator wall from the housing 102. The portion of the flexible circuit assembly 120 that contacts the wall insulator 124, e.g., the first lateral edge 322 or the second lateral edge 324 of the flexible substrate 304, can be formed from an insulating material. More particularly, the peripheral edge 1204 of the flexible substrate 304 can have no conductive traces or conductive components thereon, such that contact between the flexible circuit assembly 120 and the interior surface of the wall insulator 124 is not in electrical contact.

The physical, non-electrical, contact between the wall insulator 124 and the flexible circuit assembly 120 can stabilize the flexible circuit assembly 120 within the electronics compartment 116. When the peripheral edge 1204 of the flexible substrate 304 presses against the interior surface 204 of the wall insulator 124, the wall insulator 124 and the housing 102 that surrounds the wall insulator 124, act essentially as an external frame for the flexible circuit assembly 120. Impacts, vibrations, or other forces acting on the flexible circuit assembly 120 can be counteracted by the wall insulator 124 and the housing 102. Accordingly, physical contact between the wall insulator 124 and the flexible circuit assembly 120 can limit deflections and loading of the flexible circuit assembly 120. More particularly, stresses applied to the connector pins, e.g., the feedthrough pin 1104 and/or the battery pins 902, by the electrical connectors 308 can be limited by the external support provided by the wall insulator 124 and the housing 102. Furthermore, the external frame provided by the wall insulator 124 and the housing 102 requires fewer parts and is more space-efficient than would be the case if a separate external framework was used to support the flexible circuit assembly 120 within the electronics compartment 116. Accordingly, supporting a length of the peripheral edge 1204 of the flexible circuit assembly 120 by the wall insulator 124 and the housing 102 along an insulated (non-conductive) portion of the flexible substrate 304 provides for a robust and compact biostimulator 100.

The wall insulator and the end insulator embodiments described above are provided by way of example, and not limitation. For example, in an embodiment, the wall insulator 124 may be replaced by an insulating coating applied to the inner surface 118 of the housing 102. The insulating coating can be a conformal coating of parylene, for example, and can insulate the metallic housing 102 material from the flexible circuit assembly 120. Accordingly, the wall insulator 124 may be a separate component or integrally formed with the housing 102.

Figure 21:
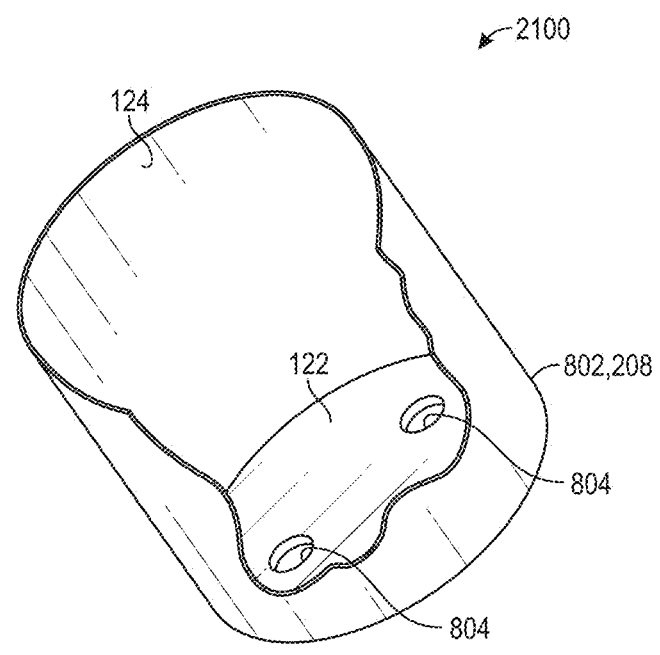
FIG. 21 is a perspective view of a cap insulator, in accordance with an embodiment.

Referring to FIG. 21, a perspective view of a cap insulator is shown in accordance with an embodiment. The wall insulator 124 and the end insulator 122 may be integrally formed. For example, the wall insulator 124 may be a tubular side wall of a cap insulator 2100, and the end insulator 122 may be a flat end of the cap insulator. The cap insulator 2100 can have the shape that results from combining the wall insulator 124 with the end insulator 122. More particularly, the cap insulator 2100 can be formed by joining an outer edge 802 of the end insulator 122 to the distal wall end 206 or the proximal wall end 208 of the wall insulator 124. The edges can be joined, e.g., by a thermal or adhesive welding process. Alternatively, the cap insulator 2100 can be formed in a molding or thermoforming process, in which the end insulator 122 and wall insulator 124 portions are integrally fabricated. Similarly, slots 804 can be formed, during or after the molding or thermoforming process, as holes in the end of the insulating cup to permit passage of electrical pins.

It will be appreciated that the cap insulator 2100 can be placed over the flexible circuit assembly 120 to constrain and isolate the flexible circuit assembly 120 from adjacent conductive components. Furthermore, several cups may be used to isolate the flexible circuit assembly 120 at both ends. For example, a first cap insulator can be used to isolate a proximal portion of the flexible circuit assembly 120, and a second cap insulator can be used to isolate a distal portion of the flexible circuit assembly 120. The cap insulators can have walls sized to overlap each other, e.g., in a sliding fit by sliding one cap wall into and over another. The cap insulators may also have holes sized to receive battery pins (in the case of the proximal cap insulator) or a feedthrough pin (in the case of the distal cap insulator. Accordingly, the cap insulators can be assembled onto each other to completely encapsulate the flexible circuit assembly 120 within an insulated cavity surrounded by the cap insulator walls and ends.

Based on the assembled structure described above, it will be appreciated that the individual components of the electrical feedthrough assembly can be fit together during assembly, e.g., during a method of manufacturing the biostimulator 100. The method can include a sequence of operations. The operations are described below in one order, which may be suitable for the flexible circuit assembly 120 having socket connectors to connect to external electrical pins. In an alternative embodiment, such as when the flexible circuit assembly 120 has metallized pads to connect to the external electrical pins, the operations may be performed in an alternative order.

In an operation, the flexible circuit assembly 120 can be folded along the fold region 316 into the stacked configuration 702. In the stacked configuration 702, the first mounting region 312 faces the second mounting region 314 in the transverse direction 325. The foam tape may optionally be placed between the mounting region faces prior to folding the flexible circuit assembly 120, and thus, may temporarily hold the flexible circuit assembly 120 in the stacked configuration 702 during the assembly process.

In an operation, the battery pins 902 can be inserted through respective slots 804 in the end insulator 122. Accordingly, the battery pins 902 can extend distally to pin tips that are separated from the distal face 904 of the battery by the end insulator 122.

In an operation, the battery pins 902 of the battery can be inserted into respective battery connectors 410 on the folded mounting surface 306. When the folded flexible circuit assembly 120 is loaded onto the battery pins 902, the longitudinal edges of the flexible substrate 304 can be at a same longitudinal location, and can be separated from the distal face 904 of the battery by the end insulator 122. Accordingly, the protective gap 704 within the interior of the folded flexible circuit assembly 120 can contain the battery pins 902 and can be separated from the battery by the end insulator 122.

In an operation, the wall insulator 124 can be disposed over and around the folded flexible circuit assembly 120. The housing 102 can be loaded over the wall insulator 124 and mounted on the battery such that the inner surface 118 of the housing 102 extends around the wall insulator 124 and the flexible circuit assembly 120. The peripheral edge 1204 of the flexible circuit assembly 120 can physically contact an interior surface of the wall insulator 124, and can press the wall insulator 124 radially outward into contact with the inner surface 118 of the housing 102. Accordingly, the housing 102 can provide an external support to the flexible circuit assembly 120.

In an operation, the feedthrough pin 1104 is inserted through the aperture 326 in the fold region 316 of the flexible circuit assembly 120. The feedthrough pin 1104 can engage the feedthrough connector 402, e.g., can insert into the socket connector, on the mounting surface 306 such that the feedthrough pin 1104 extends from a tip within the protected gap to a base outside of the protected gap. The fold region 316 of the flexible substrate 304 can separate the protected gap from the distal region of the electronics compartment 116. The battery can be hermetically sealed to the proximal end of the housing 102 by a first circumferential weld, and the header assembly 110 can be hermetically sealed to the distal end of the housing 102 by a second circumferential weld. The assembled biostimulator 100 can then be delivered and implanted at a target site to deliver pacing impulses to the target site.

FIGS. 13-16 illustrate assembly of the biostimulator 100, and more particularly, illustrate the assembly of the biostimulator 100 having flexible circuit assembly 120 that includes metallized pads 1302 to connect to the feedthrough pin 1104 and battery pins 902. It will be appreciated that the assembly operations described below may be performed in any order. For example, whereas the housing 102 may be loaded over the flexible circuit assembly 120 after the feedthrough pin 1104 is attached to the metallized pad 1302 in the following description, it will be appreciated that the housing 102 may be loaded over the flexible circuit assembly 120 before the feedthrough pin 1104 is attached to the socket connector in the embodiments described above.

Referring to FIG. 13, a cross-sectional view of a header assembly connected to a flexible circuit assembly is shown in accordance with an embodiment. In an embodiment, the feedthrough connector 402 and the battery connectors 410 are metallized pads 1302. For example, the pads can be formed on the flexible substrate 304 using semiconductor fabrication processes. The flexible circuit assembly 120 can be folded along the fold region 316 into the stacked configuration 702.

In an embodiment, the aperture axis 352 can extend between the first mounting region 312 and the second mounting region 314, e.g., over the metallized pads 1302, when the flexible circuit assembly 120 is in the stacked configuration 702. For example, the aperture axis 352 can extend parallel to the longitudinal axis 108, and in alignment with the feedthrough connector 402. More particularly, the aperture axis 352 can be between and laterally aligned with the feedthrough connector 402 and the electronic component 310 when the flexible circuit assembly 120 is in the stacked configuration 702. When laterally aligned, a transverse plane containing the aperture axis 352 and extending in the transverse direction 325 can intersect the feedthrough connector 402. Accordingly, the feedthrough pin 1104 can extend through the aperture 326 and over the feedthrough connector 402 to be placed in contact with metallized pad 1302.

In an embodiment, the feedthrough pin 1104 is spot welded to the metallized pad 1302 of the feedthrough connector 402. Alternatively, the pin can be soldered to the pad. The feedthrough pin 1104 may be shorter when the electrical connectors 308 are metallized pads 1302, as compared to when the electrical connectors 308 are socket connectors, because the spot weld, which requires minimal space, can connect the feedthrough pin 1104 to the feedthrough connector 402. The feedthrough pin 1104 can be connected to the feedthrough connector 402 prior to connecting the battery pins 902 to the battery connectors 410. For example, the feedthrough pin 1104 can be welded or soldered to the metallized pad 1302.

Referring to FIG. 14, a cross-sectional view of a header assembly and a battery connected to a flexible circuit assembly is shown in accordance with an embodiment. The battery pins 902 can be placed on corresponding metallized pads 1302 of the flexible circuit assembly 120. For example, the battery pins 902 can be inserted through respective slots 804 in the end insulator 122, and placed onto or into the battery connectors 410. The battery pins 902 can be connected to respective battery connectors 410 by respective spot welds. Alternatively, the pins may be soldered to the pads. When the battery pins 902 are attached to the respective battery connectors 410, either by a thermal weld or by inserting the pins into a spring connector as described above, the end insulator 122 can be retained between the flexible circuit assembly 120 and the distal face 904 of the battery.

Several advantages accrue from the use of the metallized pads 1302, or similar electrical connections using welded or solder construction to transmit power between the flexible circuit assembly 120 and external components, such as the energy source 107 (battery). As described above, the metallized pads 1302 use less space than socket connectors, and thus, can reduce an overall size of the biostimulator 100. Second, weld attachments can be produced at lower cost than other connectors, such as socket connectors. Third, weld attachments can be easily validated, which can improve manufacturability and contribute to long term reliability of the biostimulator 100.

In an embodiment, after the feedthrough pin 1104 is connected to the feedthrough connector 402 and the battery pins 902 are connected to the battery connectors 410, the double-sided foam tape 1202 can be disposed between the mounting surface 306. The flexible circuit assembly 120 can then be folded to press the mounting surface 306 against the foam tape 1202. Accordingly, the foam tape 1202 can hold the flexible circuit assembly 120 in the folded, or stacked, configuration.

Referring to FIG. 15, a cross-sectional view of an electronics compartment of a biostimulator containing a wall insulator and a flexible circuit assembly is shown in accordance with an embodiment. In an operation, the wall insulator 124 can be mounted over the stacked flexible circuit assembly 120. For example, the wall insulator 124 can be slid over the flange 1004 until the proximal wall end 208 contacts the end insulator 122 and/or the distal face 904 of the battery. When the wall insulator 124 is placed over the flange 1004, the distal wall end 206 can be adjacent to a proximal edge of the flange 1004, and thus, the wall insulator 124 can extend around the flexible circuit assembly 120. More particularly, the flexible circuit assembly 120 can contain the flexible circuit assembly 120 having electrical connectors 308 connected to the feedthrough 1102 and the battery.

After sliding the wall insulator 124 over the flexible circuit assembly 120, the housing 102 can be added over the wall insulator 124. More particularly, the housing 102 can be assembled over the folded flexible circuit assembly 120 to isolate and contain the electrical components. The housing 102 can slide over the flange 1004 until a proximal end of the housing 102 abuts the battery. A distal end of the housing 102, by contrast, is adjacent to the flange 1004. Accordingly, when the housing 102 is mounted on the battery, the inner surface 118 can extend around the end insulator 122, the wall insulator 124, and the flexible circuit assembly 120.

The biostimulator 100 assembly can be secured by attaching the header assembly 110, e.g., the flange 1004, to the housing 102, and by attaching the housing 102 to the battery. In an embodiment, a first circumferential weld 1502 is formed along a seam between the flange 1004 and the distal end of the housing 102. Similarly, a second circumferential weld 1504 can be formed along a seam between the housing 102 and the battery. The circumferential welds secure and seal the components. More particularly, the welds can be hermetic welds that isolate the components within the electronics compartment 116 from a surrounding environment.

In an embodiment, when the housing 102 and the wall insulator 124 are secured around the flexible circuit assembly 120, the components are tightly fit together. The peripheral edges 1204 can deflect outward, e.g., when the foam tape 1202 loses grip, and press outward against the interior surface of the wall insulator 124. In the case of the corrugated wall insulator 124, the wall insulator 124 can expand outward and press against the inner surface 118 of the housing 102. Accordingly, the wall insulator 124 may be sandwiched between the inner surface 118 of the housing 102 and the peripheral edges 1204 of the flexible circuit assembly 120.

In an embodiment, one or more of the end insulator 122 or the wall insulator 124 include an adhesive film (not shown). The adhesive film can include a pressure-sensitive or other adhesive covering one or more of the surfaces of the end insulator 122 or the wall insulator 124. For example, an interior surface of the wall insulator 124 and an upper surface of the end insulator 122 may include adhesive. Accordingly, the surfaces facing the flexible circuit assembly 120 can have adhesive, and thus, the adhesive film(s) can attach the insulators 122, 124 to the flexible circuit assembly 120. In the embodiments described above, the use of adhesive to bind the components within housing 102 to each other can facilitate several advantages. First, the adhesive can improve placement by reducing the likelihood that components will shift within the housing 102. Second, by the adhesive can ensure insulation of the electrical components. For example, by reducing the likelihood of shifting of the electronic components, formation of a gap between the insulators 122, 124 may be prevented, thereby reducing the likelihood that the electronic components of the flexible circuit assembly 120 could become exposed to an interior surface of the conductive housing 102.

Figure 16:
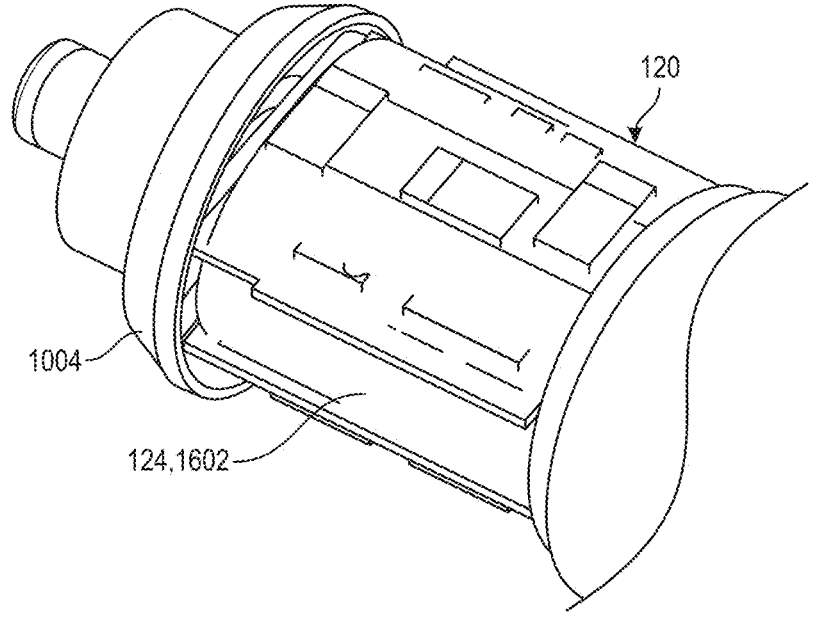
FIG. 16 is a perspective view of an electronics compartment of a biostimulator containing a wall insulator overmolded on a flexible circuit assembly, in accordance with an embodiment.

Referring to FIG. 16, a perspective view of an electronics compartment of a biostimulator containing a wall insulator overmolded on a flexible circuit assembly is shown in accordance with an embodiment. The wall insulator 124 may be overmolded onto the flexible circuit assembly 120. The overmolding operation may occur, for example, after the feedthrough pin 1104 and the battery pins 902 are connected to respective electrical connectors 308 on the flexible circuit assembly 120. An overmold 1602 may be placed over and around the components of the folded flexible circuit assembly 120. The overmold 1602 can be a polymer material, for example, and can isolate and electrically insulate the components from the housing 102. More particularly, when the housing 102 is loaded over the overmolded wall insulator 124, the overmold 1602 material can separate the electrical connectors 308 of the flexible circuit assembly 120 from the inner surface 118 of the housing 102 (not shown). The overmolded wall insulator 124, therefore, serves essentially the same function as the tubular insulating sleeve described above. The overmold 1602 can be hermetically sealed within the electronics compartment 116 by forming circumferential welds around the housing 102 at the flange 1004 and the battery, as described above.

Figure 17:
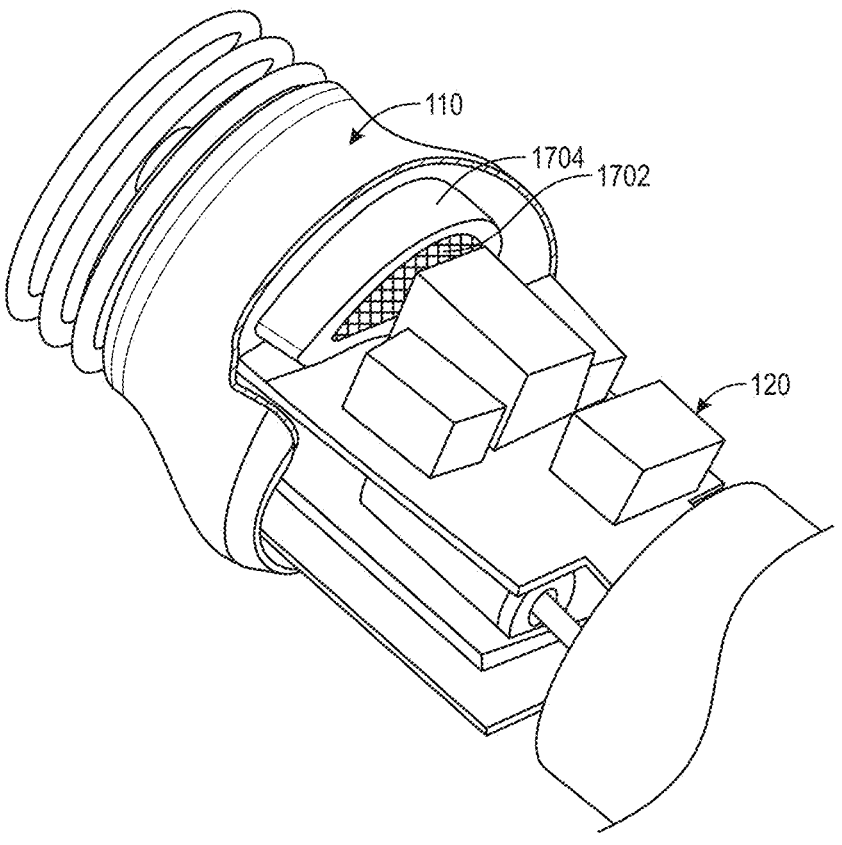
FIG. 17 is a perspective view of a moisture getter in an electronics compartment of a biostimulator, in accordance with an embodiment.

Referring to FIG. 17, a cutaway view of a moisture getter in an electronics compartment of a biostimulator is shown in accordance with an embodiment. The electronics compartment 116 can be hermetically sealed within the biostimulator 100. For example, the header assembly 110 can be joined to a distal end of the housing 102 (not shown) by a hermetic weld around a circumference of the distal end. Similarly, the battery can be joined to a proximal end of the housing 102 (not shown) by hermetic weld around a circumference of the proximal end. Accordingly, any moisture trapped within the electronics compartment 116 during the manufacturing process may remain there unless steps are taken to eliminate the moisture.

In an embodiment, the biostimulator 100 includes a moisture getter 1702 within the electronics compartment 116. The moisture getter 1702 can be a desiccant that absorbs residual moisture within the electronics compartment 116. The moisture getter 1702 can include the desiccant within a permeable matrix, such as a polymer. An example of a suitable desiccant material includes zeolite, however, other desiccants may be used in the moisture getter 1702.

The moisture getter 1702 can be loaded into and retained by the getter holder 1704. The getter holder 1704 can be mounted on a component within the electronics compartment 116, such as on a proximal face or surface of the header assembly 110. The getter holder 1704 can occupy space within the electronics compartment 116 without interfering with the components of the flexible circuit assembly 120.

Figure 18:
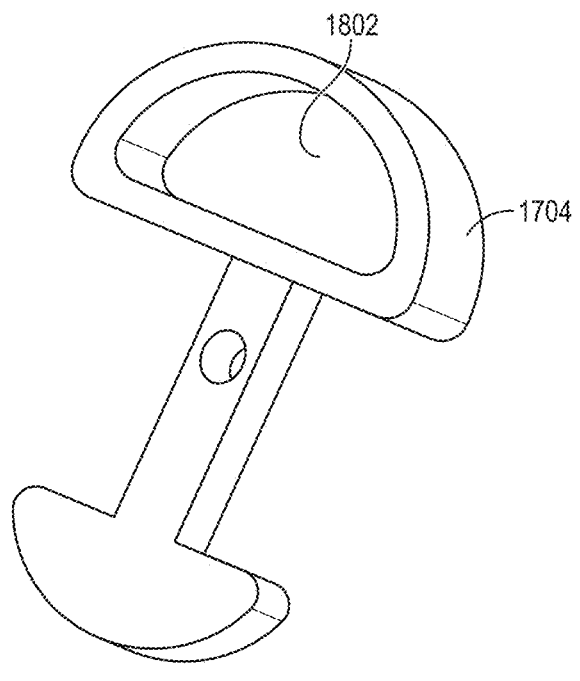
FIG. 18 is a perspective view of a moisture getter holder, in accordance with an embodiment.

Referring to FIG. 18, a perspective view of a moisture getter holder is shown in accordance with an embodiment. The getter holder 1704 can include a cavity 1802. For example, the cavity 1802 can be a recess machined or otherwise formed in a surface of the getter holder 1704 to allow sufficient moisture getter 1702 to be loaded within the cavity 1802 to scavenge moisture from the electronics compartment 116. In an embodiment, the cavity 1802 has a volume of 1.5-2.5 mm3, e.g., 1.9 mm3, to contain a corresponding volume of moisture getter material. The moisture getter 1702 can be loaded, e.g., injected, into the cavity 1802. In an embodiment, the cavity 1802 has an opening that faces proximally within the electronics compartment 116. For example, the getter holder 1704 can be fastened to the header assembly 110 such that the opening of the cavity 1802 faces toward the battery. Alternatively, the getter holder 1704 can be mounted in a proximal region of the electronics compartment 116, and the opening of the cavity 1802 can face toward the header assembly 110.

In an embodiment, the getter holder 1704 is fabricated from a low moisture material. For example, the getter holder 1704 can be machined from a glass-reinforced epoxy laminate material. Alternatively, the getter holder 1704 can be molded from a thermoset polymer, a ceramic material, or other low moisture materials.

Figure 19:
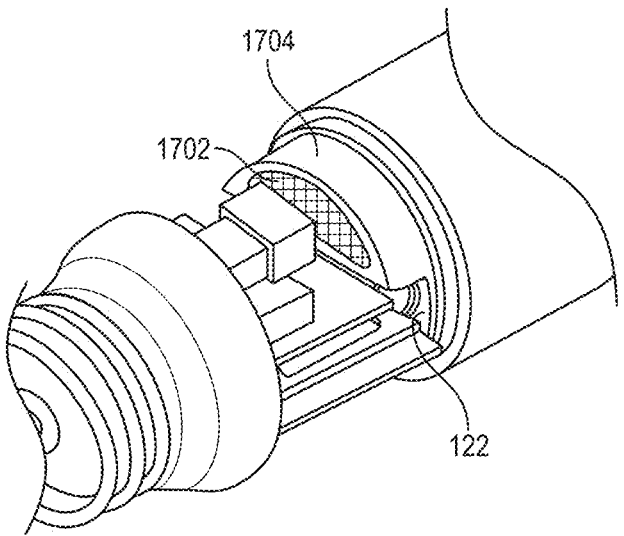
FIG. 19 is a perspective view of a moisture getter in an electronics compartment of a biostimulator, in accordance with an embodiment.

Referring to FIG. 19, a perspective view of a moisture getter in an electronics compartment of a biostimulator is shown in accordance with an embodiment. Rather than being a separate component, the getter holder 1704 can be integrated with another component of the biostimulator 100. For example, the getter holder 1704 can be fastened to or integrally formed with the end insulator 122. In an embodiment, the getter holder 1704 is bonded to a distal face of the end insulator 122, and the opening of the cavity 1802 containing the moisture getter 1702 can face in the distal direction toward the header assembly 110.

Figure 20:
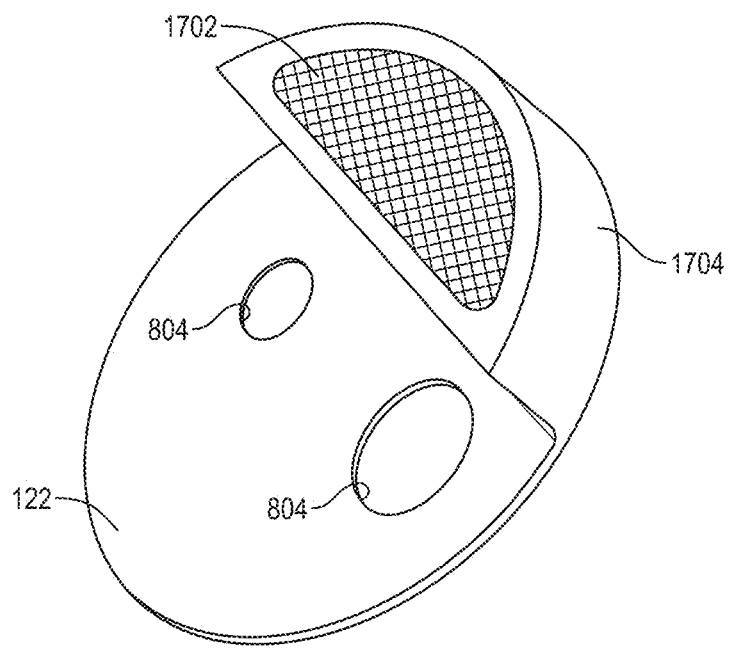
FIG. 20 is a perspective view of a moisture getter holder, in accordance with an embodiment.

Referring to FIG. 20, a perspective view of a moisture getter holder is shown in accordance with an embodiment. The getter holder 1704 may be integrally formed with the end insulator 122. For example, the end insulator 122 may have a planar proximal face and a non-planar distal face. Rather than having a planar distal face, the getter holder 1704 can be a trough that extends from the distal face 904. The integrally formed end insulator 122 can separate the battery from the flexible circuit assembly 120, and can hold the moisture getter 1702. As described above, the integrally formed end insulator 122 can include slots 804 to receive the battery pins 902. In an embodiment, the getter holder portion of the end insulator 122 and the flat portion of the end insulator 122 having the slots 804 can be formed from a glass-reinforced epoxy laminate material, or another material having low moisture and electrically insulating properties. Accordingly, the end insulator 122 can facilitate scavenging moisture from the electronics compartment 116 and can reduce a likelihood of electrical short-circuiting between the flexible circuit assembly components and other biostimulator components.

Figure 22:
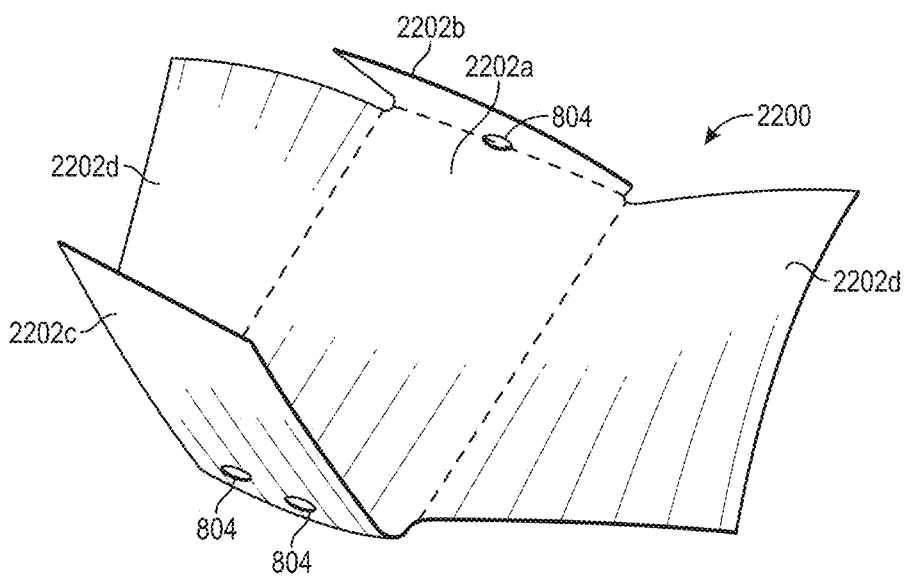
FIG. 22 is a perspective view of an insulating shroud, in accordance with an embodiment.

Alternative insulating structures used to isolate the flexible circuit assembly 120 from the housing 102 are contemplated within the scope of this description. Referring to FIG. 22, a perspective view of an insulating shroud is shown in accordance with an embodiment. An insulating shroud 2200 can be an insulator, e.g., a thin sheet of polyimide or another insulating material, having one or more foldable sections 2202. The foldable sections 2202 can be rectangular, or other-shaped, sections that are joined along respective fold lines (dotted lines). In an embodiment, the foldable sections 2202 fold relative to each other to wrap around the flexible circuit assembly 120 and to isolate the electronic components from surrounding structures. For example, a first fold section 2202a can be apposed to the first mounting region 312 during assembly, when the flexible circuit assembly 120 is in a folded configuration. One or more additional fold sections, such as a top fold section 2202b and/or a bottom fold section 2202c can then be folded along respective fold lines to cause the wings to wrap over a top end and a bottom end of the folded circuit assembly, and to appose the second mounting region 314. Optionally, one or more side fold sections 2202d can then be folded along respective fold lines to cause the wings to wrap around the sides of the folded circuit assembly. Accordingly, the wings of the insulating shroud 2200 can fold around the electronic components to encapsulate the flexible circuit assembly 120 and isolate the electronic components from the housing 102. The slots 804 can be formed in the insulating shroud 2200 to receive a feedthrough pin or battery pins. The slots 804 can be located in the insulating sheet of material along the fold lines that distinguish the first fold section 2202a from an adjacent fold section.

Several embodiments, which have been described above, are summarized in the following paragraphs. In an embodiment, a flexible circuit assembly for a biostimulator includes a flexible substrate. The flexible substrate includes a mounting surface having a fold region between a first mounting region and a second mounting region. The flexible substrate is configured to fold along the fold region into a stacked configuration such that the first mounting region faces the second mounting region. The flexible substrate includes an aperture in the fold region having an aperture axis.

The flexible circuit assembly may include a feedthrough connector on the mounting surface. When the flexible substrate is in the stacked configuration the aperture axis can extend between the first mounting region and the second mounting region in alignment with the feedthrough connector. The flexible circuit assembly may include an electronic component on the mounting surface.

The feedthrough connector may be on the first mounting region and the electronic component may be on the second mounting region.

The aperture may be centered on the mounting surface.

The flexible circuit assembly may include several battery connectors on the mounting surface.

The feedthrough connector and the several battery connectors may be socket connectors having respective socket axes extending parallel to each other. The socket axis of the feedthrough connector may be laterally between the socket axes of the battery connectors. The feedthrough connector and the several battery connectors may be metallized pads.

In an embodiment, a biostimulator includes a housing having an inner surface extending around an electronics compartment. The biostimulator includes a flexible circuit assembly within the electronics compartment. The flexible circuit assembly includes a flexible substrate including a mounting surface having a fold region between a first mounting region and a second mounting region. The flexible substrate is folded along the fold region such that the first mounting region faces the second mounting region. The flexible substrate includes an aperture in the fold region. The aperture has an aperture axis. The flexible circuit assembly includes a feedthrough connector on the mounting surface. The aperture axis extends in alignment with the feedthrough connector. The flexible circuit assembly includes an electronic component on the mounting surface.

The feedthrough connector may be on the first mounting region and the electronic component may be on the second mounting region such that the feedthrough connector and the electronic component are in a stacked configuration.

The aperture may be centered on the mounting surface.

The biostimulator may include a foam tape between the feedthrough connector and the electronic component.

The biostimulator may include a battery having several battery pins extending from a distal face in a longitudinal direction. The flexible circuit assembly includes several battery connectors connected to respective battery pins of the battery. The battery pins have respective pin axes extending parallel to the aperture axis of the aperture. The biostimulator may include an end insulator between the distal face of the battery and the flexible circuit assembly. The end insulator may be planar and may include several slots. The several battery pins may extend through the several slots into the electronics compartment. The end insulator may have an outer edge. The outer edge and the inner surface of the housing may have a same profile.

The biostimulator may include a wall insulator extending around the flexible circuit assembly within the electronics compartment.

The biostimulator may include a moisture getter within the electronics compartment.

In an embodiment, a method includes folding a flexible circuit assembly along a fold region into a stacked configuration. The flexible circuit assembly includes a mounting surface having the fold region between a first mounting region and a second mounting region. The first mounting region faces the second mounting region in a transverse direction when the flexible circuit assembly is in the stacked configuration. The method includes connecting a feedthrough pin to a feedthrough connector on the mounting surface between the first mounting region and the second mounting region. The feedthrough pin extends through an aperture in the fold region. The method includes connecting several battery pins of a battery to respective battery connectors on the mounting surface.

The method may include inserting the several battery pins through respective slots in an end insulator. The end insulator may be between the battery and the flexible circuit assembly when the several battery pins are attached to the respective battery connectors. The method may include mounting a wall insulator over the stacked flexible circuit assembly such that the wall insulator extends around the flexible circuit assembly. The method may include mounting a housing on the battery such that an inner surface of the housing extends around the end insulator, the wall insulator, and the flexible circuit assembly. The wall insulator may be sandwiched between the inner surface of the housing and peripheral edges of the flexible circuit assembly. The method may include attaching the housing to a header assembly and the battery to contain an electronics compartment between the battery, the inner surface of the housing, and the header assembly. The flexible circuit assembly may be within the electronics compartment. The header assembly may include a feedthrough having the feedthrough pin, an electrode tip, and a fixation element.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A biostimulator, comprising:
a housing having an electronics compartment and an inner surface extending around the electronics compartment;
a flexible circuit assembly within the electronics compartment; and

a wall insulator extending around the flexible circuit assembly within the electronics compartment, wherein the wall insulator includes a cylindrical sleeve disposed radially between the flexible circuit assembly and the inner surface of the housing within the electronics compartment to separate and electrically insulate the flexible circuit assembly from the housing;
wherein a wall interior surface of the wall insulator is in contact with an exterior of the flexible circuit assembly to stabilize the flexible circuit assembly within the electronics compartment.

2. The biostimulator of claim 1, wherein the wall insulator is sandwiched between peripheral edges of the flexible circuit assembly and the housing.

3. The biostimulator of claim 1, wherein the wall insulator has a tubular structure.

4. The biostimulator of claim 3, wherein a cross-sectional profile of the tubular structure is circular.

5. The biostimulator of claim 1, wherein the wall interior surface includes an adhesive coating.

6. The biostimulator of claim 1, wherein the wall insulator includes a dielectric material.

7. The biostimulator of claim 1, wherein the flexible circuit assembly includes a mounting surface having a fold region between a first mounting region and a second mounting region, wherein the flexible circuit assembly is configured to fold along the fold region into a stacked configuration so that the first mounting region faces the second mounting region, and wherein the flexible circuit assembly includes an aperture in the fold region.

8. The biostimulator of claim 7 further comprising a processor and a feedthrough connector on the mounting surface, wherein the processor is configured to control generation of a pacing impulse, and wherein the feedthrough connector is configured to receive the pacing impulse and to transmit the pacing impulse through the aperture to a target tissue.

9. The biostimulator of claim 1 further comprising a header assembly and a battery, wherein the housing is mounted on the battery and the header assembly is mounted on the housing so that the flexible circuit assembly and the wall insulator are enclosed between the header assembly, the housing, and the battery.

10. A method, comprising:
connecting a plurality of battery connectors of a flexible circuit assembly to a plurality of battery pins of a battery, wherein the flexible circuit assembly is to fit within an electronics compartment of a housing; and
inserting a wall insulator over the flexible circuit assembly such that the wall insulator extends around the flexible circuit assembly, wherein the wall insulator includes a cylindrical sleeve to be disposed radially between the flexible circuit assembly and an inner surface of the housing within the electronics compartment to separate and electrically insulate the flexible circuit assembly from the housing and wherein a wall interior surface of the wall insulator is in contact with an exterior of the flexible circuit assembly to stabilize the flexible circuit assembly within the electronics compartment.

11. The method of claim 10 further comprising mounting the housing on the battery such that an inner surface of the housing extends around the electronics compartment, and the flexible circuit assembly and the wall insulator are within the electronics compartment.

12. The method of claim 11 further comprising mounting a header assembly on the housing such that the flexible circuit assembly and the wall insulator are enclosed between the header assembly, the housing, and the battery.

13. The method of claim 11, wherein the wall insulator is sandwiched between the inner surface of the housing and peripheral edges of the flexible circuit assembly.

14. The method of claim 10 further comprising folding the flexible circuit assembly along a fold region into a stacked configuration, wherein the flexible circuit assembly includes a mounting surface having the fold region between a first mounting region and a second mounting region, and wherein the first mounting region faces the second mounting region in a transverse direction when the flexible circuit assembly is in the stacked configuration.

15. The method of claim 10, wherein a wall interior surface of the wall insulator is in contact with an exterior of the flexible circuit assembly.

16. The method of claim 15, wherein the wall interior surface includes an adhesive coating.

17. A leadless cardiac pacemaker, comprising:

a housing having an electronics compartment and an inner surface extending around the electronics compartment;

a header assembly mounted on the housing, wherein the header assembly includes a pacing electrode;

a flexible circuit assembly within the electronics compartment, wherein the flexible circuit assembly includes one or more electronic components electrically connected to the pacing electrode; and a wall insulator extending around the flexible circuit assembly within the electronics compartment, wherein the wall insulator includes a cylindrical sleeve disposed radially between the flexible circuit assembly and the inner surface of the housing within the electronics compartment to separate and electrically insulate the flexible circuit assembly from the housing;

wherein a wall interior surface of the wall insulator is in contact with an exterior of the flexible circuit assembly to stabilize the flexible circuit assembly within the electronics compartment.

18. The leadless cardiac pacemaker of claim 17, wherein the wall insulator is sandwiched between peripheral edges of the flexible circuit assembly and the housing.

19. The leadless cardiac pacemaker of claim 17, wherein the wall insulator has a tubular structure.

* * * * *